United States Patent
Laayoun et al.

(10) Patent No.: US 7,691,635 B2
(45) Date of Patent: Apr. 6, 2010

(54) LABELING REAGENTS, METHODS FOR THE SYNTHESIS OF SUCH REAGENTS AND METHODS FOR THE DETECTION OF BIOLOGICAL MOLECULES

(75) Inventors: Ali Laayoun, Toussieu (FR); Eloy Bernal-Mendez, Saint Quentin Fallavier (FR)

(73) Assignee: Biomerieux, Marcy l'Etoile (FR)

( * ) Notice: Subject to any disclaimer, the term of this patent is extended or adjusted under 35 U.S.C. 154(b) by 228 days.

(21) Appl. No.: 10/590,973

(22) PCT Filed: Mar. 24, 2005

(86) PCT No.: PCT/FR2005/050192

§ 371 (c)(1),
(2), (4) Date: Aug. 28, 2006

(87) PCT Pub. No.: WO2005/092910

PCT Pub. Date: Oct. 6, 2005

(65) Prior Publication Data

US 2008/0032288 A1 Feb. 7, 2008

(30) Foreign Application Priority Data

Mar. 26, 2004 (FR) .................................. 04 50600

(51) Int. Cl.
| | |
|---|---|
| G01N 37/00 | (2006.01) |
| G01N 33/48 | (2006.01) |
| C07D 239/70 | (2006.01) |
| A61K 31/4188 | (2006.01) |

(52) U.S. Cl. .................... 436/56; 436/63; 436/501; 436/544; 436/546; 535/6; 536/23.1; 548/304.1; 514/393

(58) Field of Classification Search .................. 436/56, 436/63, 501, 544, 546; 535/6; 536/23.1; 548/304.1; 514/393

See application file for complete search history.

(56) References Cited

U.S. PATENT DOCUMENTS

| | | |
|---|---|---|
| 4,507,466 A | 3/1985 | Tomalia et al. |
| 4,568,737 A | 2/1986 | Tomalia et al. |
| 4,672,040 A | 6/1987 | Josephson |
| 4,683,195 A | 7/1987 | Mullis et al. |
| 4,683,202 A | 7/1987 | Mullis |
| 4,775,745 A | 10/1988 | Ford et al. |
| 4,800,159 A | 1/1989 | Mullis et al. |
| 5,234,809 A | 8/1993 | Boom et al. |
| 5,328,824 A | 7/1994 | Ward et al. |
| 5,399,491 A | 3/1995 | Kacian et al. |
| 5,449,767 A | 9/1995 | Ward et al. |
| 5,489,653 A | 2/1996 | Charles et al. |

(Continued)

FOREIGN PATENT DOCUMENTS

DE 3.910.151 A1 10/1990

(Continued)

OTHER PUBLICATIONS

T.W. Greene et al., Protective Groups in Organic Synthesis, 3rd Edition, John Wiley and Sons, Inc., New York (1991), pp. 230-245.

(Continued)

*Primary Examiner*—Kamal A Saeed
*Assistant Examiner*—Michael Barker
(74) *Attorney, Agent, or Firm*—Oliff & Berridge, PLC

(57) ABSTRACT

The present invention relates to a temperature-stable labeling reagent of formula (0):

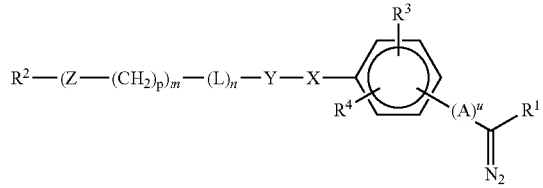

in which:
$R^1$ represents H or an alkyl, aryl or substituted aryl group,
$R^2$ represents a detectable marker or at least two detectable markers interlinked by at least one multimeric structure,
L is a linker arm comprising a linear chain of at least two covalent bonds and n is an integer equal to 0 or 1,
$R^3$ and $R^4$ represent, independently of one another: H, $NO_2$, Cl, Br, F, I, $R^2\text{-}(L)_n\text{-}Y\text{-}X\text{-}$, OR, SR, $NR_2$, R, NHCOR, CONHR, COOR, $-CO-NH-(CH_2)_3-(O-CH_2-CH_2)_3-CH_2-NH-R^2$, $-CO-NH-(CH_2)_3-(O-CH_2-CH_2)_4-CH_2-NH-R^2$ with R=alkyl or aryl,
A is a linker arm comprising at least one covalent double bond enabling the conjugation of the diazo function with the aromatic ring and u is an integer between 0 and 2, preferably 0 or 1,
$-Y-X-$ represents $-CONH-$, $-NHCO-$, $-CH_2O-$, $-CH_2S-$,
$-Z-$ represents $-NH-$, $-NHCO-$, $-CONH-$ or $-O-$,
m is an integer between 1 and 10, preferably between 1 and 3, and
p is an integer between 1 and 10, preferably between 1 and 3.

The present invention also describes a method for the synthesis of said labels and also applications for the labeling of biological molecules, in particular of nucleic acids, with a labeling reagent bearing the diazomethyl function.

The invention is particularly suitable for use in the field of diagnostics.

41 Claims, 2 Drawing Sheets

U.S. PATENT DOCUMENTS

| | | | |
|---|---|---|---|
| 5,695,936 | A | 12/1997 | Mandrand et al. |
| 5,750,338 | A | 5/1998 | Collins et al. |
| 6,033,853 | A | 3/2000 | Delair et al. |
| 6,083,708 | A | 7/2000 | Singh et al. |
| 6,083,762 | A | 7/2000 | Papen et al. |
| 6,083,763 | A | 7/2000 | Balch |
| 6,110,426 | A | 8/2000 | Shalon et al. |
| 6,133,047 | A | 10/2000 | Elaissari et al. |
| 6,376,179 | B1 | 4/2002 | Laayoun |
| 6,489,114 | B2 | 12/2002 | Laayoun et al. |
| 6,521,341 | B1 | 2/2003 | Elaissari et al. |
| 6,537,783 | B1 | 3/2003 | Guillou-Bonnici et al. |
| 6,576,448 | B2 | 6/2003 | Weissman et al. |
| 6,632,662 | B1 | 10/2003 | Broyer et al. |
| 6,660,472 | B1 | 12/2003 | Santoro et al. |
| 6,686,195 | B1 | 2/2004 | Colin et al. |
| 6,818,398 | B2 | 11/2004 | Bavykin et al. |
| 6,875,858 | B1 | 4/2005 | DeFrancq et al. |
| 7,338,805 | B2 * | 3/2008 | Bourget et al. ............ 436/56 |
| 2002/0081586 | A1 | 6/2002 | Laayoun et al. |
| 2002/0155496 | A1 | 10/2002 | Charles et al. |
| 2004/0005614 | A1 | 1/2004 | Kurn et al. |
| 2004/0091451 | A1 | 5/2004 | Charreyre et al. |
| 2008/0032288 | A1 | 2/2008 | Laayoun et al. |

FOREIGN PATENT DOCUMENTS

| | | |
|---|---|---|
| EP | 0.063.879 A2 | 11/1982 |
| EP | 0.097.373 A2 | 1/1984 |
| EP | 0 201 184 A2 | 12/1986 |
| EP | 0.286.898 A2 | 10/1988 |
| EP | 0.302.175 A2 | 2/1989 |
| EP | 0.329.198 A2 | 8/1989 |
| EP | 0.350.407 B1 | 1/1990 |
| EP | 0.561.722 A1 | 9/1993 |
| EP | 0.567.841 A2 | 11/1993 |
| EP | 0.569.272 B1 | 11/1993 |
| EP | 0.669.991 B1 | 9/1995 |
| EP | 0.827.552 B1 | 3/1998 |
| FR | 2 607 507 | 6/1988 |
| WO | WO 88/04289 A1 | 6/1988 |
| WO | WO 90/01069 A1 | 2/1990 |
| WO | WO 90/06995 A1 | 6/1990 |
| WO | WO 90/08838 A1 | 8/1990 |
| WO | WO 99/53304 A1 | 10/1990 |
| WO | WO 91/02818 A1 | 3/1991 |
| WO | WO 93/16094 A2 | 8/1993 |
| WO | WO 95/08000 A2 | 3/1995 |
| WO | WO 97/35031 A1 | 9/1997 |
| WO | WO 97/45202 A1 | 12/1997 |
| WO | WO 98/05766 A1 | 2/1998 |
| WO | WO 99/15621 A1 | 4/1999 |
| WO | WO 99/35500 A1 | 7/1999 |
| WO | WO 99/65926 A1 | 12/1999 |
| WO | WO 00/05338 A1 | 2/2000 |
| WO | WO 00/07982 A1 | 2/2000 |
| WO | WO 00/40590 A2 | 7/2000 |
| WO | WO 00/60049 A1 | 10/2000 |
| WO | WO 01/44506 A1 | 6/2001 |
| WO | WO 01/92361 A1 | 12/2001 |
| WO | WO 02/090319 A1 | 11/2002 |
| WO | WO 02/090584 A2 | 11/2002 |
| WO | WO 2005/092910 A1 | 10/2005 |

OTHER PUBLICATIONS

S. Hunt, "The Non-Protein Amino Acids," Chemistry and Biochemistry of the Amino Acids, edited by G.C. Barett, Chapman and Hall, London (1985), pp. 55-138.

M. O'Donnell et al., "Reporter Groups for the Analysis of Nucleic Acid Structure," Bioorganic Chemistry: Nucleic Acids, Oxford University Press (1996), pp. 216-243.

J. Randolph et al., "Stability, Specificity and Fluorescence Brightness of Multiply-labeled Fluorescent DNA Probes," Nucleic Acids Research (1997), vol. 25, No. 14, pp. 2923-2929.

T. Livache et al., "Preparation of a DNA Matrix Via an Electrochemically Directed Copolymerization of Pyrrole and Oligonucleotides Bearing a Pyrrole Group," Nucleic Acids Research (1994), vol. 22, No. 15, 2915-2921.

J. Cheng et al., "Preparation and Hybridization Analysis of DNA/ RNA from E. coli on Microfabricated Bioelectronic Chips," Nature Biotechnology, vol. 16 (1998), pp. 541-546.

T. Okamoto et al., "Microarray Fabrication with Covalent Attachment of DNA Using Bubble Jet Technology," Nature Biotechnology, vol. 18 (2000), pp. 438-441.

G. Ramsay, "DNA Chips: State-of-the Art," Nature Biotechnology, vol. 16 (1998), pp. 40-44.

J. Cheng et al., "Microchip-based Devices for Molecular Diagnosis of Genetic Diseases," Molecular Diagnosis, vol. 1, No. 3 (1996), pp. 183-200.

T. Holton et al., "Advantageous Syntheses of Diazo Compounds by Oxidation of Hydrazones with Lead Tetraacetate in Basic Environments," J. Org. Chem. (1995), vol. 60, pp. 4725-4729.

A. Laayoun et al., "Aryldiazomethanes for Universal Labeling of Nucleic Acids and Analysis on DNA Chips," Bioconjugate Chem. (2003), vol. 14, pp. 1298-1306.

M. Shiga et al., "Synthesis of a Novel Biotin Derivative That Bears a Diazo Group as the Reactive Site," Analytical Sciences (1993), vol. 9, pp. 553-556.

M. Shiga et al., "Fluorescence Detection of DNA Using a Novel Peroxidase Substrate, 4-(4-Hydroxyphenylcarbamoyl)butanoic Acid," Analytical Sciences (1995), vol. 11, pp. 591-595.

P. Langer et al., "Enzymatic Synthesis of Biotin-labeled Polynucleotides: Novel Nucleic Acid Affinity Probes," Proc. Natl. Acad. Sci. USA, vol. 78, No. 11 (1981), pp. 6633-6637.

E. Bayer et al., "The Use of the Avidin-Biotin Complex as a Tool in Molecular Biology," Methods of Biochemical Analysis, vol. 26 (1980), pp. 1-45.

G. Pratviel et al., "Carbon-Hydrogen Bonds of DNA Sugar Units as Targets for Chemical Nucleases and Drugs," Angew. Chem. Int. Ed. Engl., vol. 34 (1995), pp. 746-769.

D. Sigman et al., "Chemical Nucleases," Chem. Rev., vol. 93 (1993), pp. 2295-2316.

"2 Methods for the Preparation of Alkane, Alkene, and Alkyne Diazo Compounds," pp. 34-48, 1995.

B. Charleux et al., "Radical-initiated Copolymers of Styrene and p-Formylstyrene, 1 Solution Copolymerization and Characterization," Makromol. Chem., vol. 193 (1992), pp. 187-203.

M. Egholm et al., "Peptide Nucleic Acids (PNA) Oligonucleotide Analogues with an Achiral Peptide Backbone," J. Am. Chem. vol. 114 (1992), pp. 1895-1897.

W. Jencks et al., "Reactivity of Nucleophilic Reagents toward Esters," J. Amer. Chem Soc., vol. 82 (1960), pp. 1778-1786.

G. Pratviel et al., "DNA and RNA Cleavage by Metal Complexes," Adv. Org. Chem., vol. 45 (1998), pp. 251-312.

F. Ginot, "Oligonucletide Micro-Arrays for Identification of Unknown Mutations: How Far from Reality?," Human Mutation, vol. 10 (1997), pp. 1-10.

X. Creary, "Tosylhydrazone Salt Pyrolyses: Phenyldiazomethanes," Organic Synthesis, Coll., vol. 7 (1990), pp. 438-443.

M. Oivanen et al., "Kinetics and Mechanisms for the Cleavage and Isomerization of the Phosphodiester Bonds of RNA by Bronsted Acids and Bases," Chem. Rev., vol. 98 (1998), pp. 961-990.

S. Agrawal, "Protocols for Oligonucleotides and Analogs, Synthesis and Properties," Methods in Molecular Biology, vol. 20, Humana Press, New Jersey, 1993.

S. Wong, "Chemistry of Protein Conjugation and Cross-Linking," CRC Press (1991) pp. 16-45.

G. M. Makrigiorgos et al., "Fluorescent Labeling of Abasic Sites: A Novel Methodology to Detect Closely-Spaced Damage Sites in DNA," Int. J. Radiat. Biol. (1998), vol. 74, No. 1, pp. 99-109.

W. C. Still et al., "Rapid Chromatographic Technique for Preparative Separations with Moderate Resolution," J. Org. Chem. (1978), vol. 43, No. 14, pp. 2923-2925.

A. Troesch et al., "Mycobacterium Species Identification and Rifampin Resistance Testing with High-Density DNA Probe Arrays," Journal of Clinical Microbiology (Jan. 1990), vol. 37, No. 1, pp. 49-55.

Jul. 25, 2002 International Search Report issued in International Application No. PCT/FR02/01543.

Jan. 14, 2009 International Search Report issued in International Application No. PCT/FR2008/051026.

Jul. 30, 2004 Office Action issued in U.S. Appl. No. 10/137,454, now U.S. Patent No. 7,338,805 B2.

Feb. 23, 2005 Office Action issued in U.S. Appl. No. 10/137,454, now U.S. Patent No. 7,338,805 B2.

Jul. 11, 2005 Office Action issued in U.S. Appl. No. 10/137,454, now U.S. Patent No. 7,338,805 B2.

Feb. 6, 2006 Office Action issued in U.S. Appl. No. 10/137,454, now U.S. Patent No. 7,338,805 B2.

Mar. 29, 2007 Office Action issued in U.S. Appl. No. 10/137,454, now U.S. Patent No. 7,338,805 B2.

Mar. 18, 2005 Office Action issued in U.S. Appl. No. 10/137,460, now U.S. Patent No. 7,060,441 B2.

* cited by examiner

*m*-bio-TETA-PMDAM (13)

*o*-bio-TETA-PMDAM (14)

*p*-bio-TETA-PMDAM (15)

LABELING REAGENTS, METHODS FOR THE SYNTHESIS OF SUCH REAGENTS AND METHODS FOR THE DETECTION OF BIOLOGICAL MOLECULES

The present invention relates to novel reagents for labeling biological molecules, to a method for the synthesis of said labels and to applications for the labeling of biological molecules, in particular in the field of diagnosis using nucleic acid analysis.

The prior art shows that numerous methods exist for labeling nucleotides, oligonucleotides or nucleic acids.

A first method consists in attaching the label to the base, whether the latter is natural or modified. A second method proposes attaching the label to the sugar, here again whether it is natural or modified. A third method aims to attach the label to the phosphate.

Labeling on the base has in particular been used in the approach consisting in labeling the nucleic acids by incorporation of directly labeled nucleotides.

Labeling on the sugar is often used in the case of nucleic acid probes prepared by chemical synthesis.

Labeling on the phosphate has also been used to introduce functionalized arms and markers during the chemical synthesis of oligonucleotides.

In fact, those skilled in the art, who must perform labeling of a nucleotide, or of a nucleotide analog or of a nucleic acid, are inclined to carry out this attachment to the base or to the sugar, which offer them greater convenience and more alternatives. This is, moreover, what emerges from the study of numerous documents, such as EP-A-0.329.198, EP-A-0.302.175, EP-A-0.097.373, EP-A-0.063.879, U.S. Pat. No. 5,449,767, U.S. Pat. No. 5,328,824, WO-A-93/16094, DE-A-3.910.151, EP-A-0.567.841 for the base or EP-A-0.286.898 for the sugar.

The attachment of the label to the phosphate is a technique which is more complex than the technique consisting in functionalizing the base or the sugar and has been used to a much lesser extent, in particular due to the weak reactivity of the phosphate (see, for example, Jencks W. P. et al. J. Amer. Chem Soc., 82, 1778-1785, 1960). Similarly, in the review by O'Donnel and Mc Laughlin (<< Reporter groups for the analysis of nucleic acid structure >>, p 216-243, in << Bioorganic Chemistry: Nucleic Acids>>, Ed Hecht S. M., Oxford University Press, 1996) relating to methods for introducing probes into oligonucleotide fragments, effective alkylation of the internucleotide phosphodiester is considered to be impossible.

Patent application WO-A-99/65926 describes a method for labeling a synthetic or natural ribonucleic acid (RNA) which consists in fragmenting the RNA and in labeling at the end phosphate. This document describes a certain number of functions which can be used for the labeling in connection with the fragmentation, such as hydroxyl, amine, hydrazine, alkoxyamine, alkyl halide, benzyl-type alkyl halide, in particular the 5-(bromomethyl)fluorescein derivative. These functions make it possible to label nucleic acids, but it is necessary to combine a fragmentation step in order to have efficient labeling because this labeling takes place on the phosphate freed during fragmentation. Furthermore, a large excess of labeling reagent compared with the RNA must be added in order to obtain efficient labeling, which brings about problems of background noise generated by the excess label. Finally, this method does not function efficiently on double-stranded DNA.

There exists therefore a need for novel reagents which are efficient from the point of view of labeling yield, which are specific at the level of the labeling position and in particular which do not affect the properties of hybridization of the bases involved in the formation of the double helix, by means of hydrogen bonds, which can be used both for DNA and RNA and, finally, which allow labeling, without distinction, of nucleotides, oligonucleotides or nucleic acids which may be natural or prepared by enzymatic amplification.

The Applicant has already proposed such novel labels which satisfy the abovementioned conditions and which use the diazomethyl function as reactive function for the labeling. This is, for example, the case in patent applications WO-A-02/090319 and WO-A-02/090584 or in the article by Laayoun et al., published in Bioconjugate Chem. 2003, 14, 1298-1306 and entitled: "Aryldiazomethanes for Universal Labelling of Nucleic Acids and Analysis on DNA Chips", to which the reader may refer in order to understand the methods of synthesis and of use of such constituents more clearly.

Thus, the diazomethyl function (of formula —$C(N_2)$—) has already been used for the alkylation of phosphate groups, but a certain number of problems arise. Firstly, reagents which incorporate at least one diazo function are generally unstable by themselves, which poses problems for the use of these reagents in a labeling kit, which is totally unacceptable if the function of the labeled product is to demonstrate the presence of a target biological molecule in any sample.

Finally, reagents bearing the diazomethyl function and associated with certain labels, such as biotin, are relatively water-insoluble, which leads to the use of organic solvents which are water-miscible for the coupling with biological molecules, which are soluble only in water or aqueous buffers, but these solvents, present in high concentrations in the labeling reaction, slow down the reaction rate and therefore adversely affect the coupling efficiency.

The labeling reagents recommended by documents WO-A-02/090319 and WO-A-02/090584 mentioned above also solve these technical problems. The content of these applications is incorporated herein for reference.

However, even though these molecules and labeling methods are particularly efficient, the Applicant has succeeded in finding novel molecules and novel methods which further improve the labeling efficiency. The invention consists of the use of polyaminated arms which, like ethylene glycol arms, make it possible to distance the biotin from the reactive center (diazo function). Thus, a better solubility in aqueous medium is obtained through the introduction of the hydrophilic arm, with the possibility of protonation of the amines in an aqueous medium at neutral pH, which produces an attraction between the nucleic acids, which are negatively charged, and the label, with two main consequences:

more rapid labeling, which may be particularly advantageous for samples at low concentration, and stabilization of the double helix by neutralization of the negative charges of the phosphates.

Furthermore, these novel molecules make it possible to carry out methods which can function in an acidic medium, which is particularly advantageous for molecules which incorporate diazo functions. Thus, the selectivity of the reagents bearing a diazo function is therefore greater in an acid medium. The solubility introduced into the polyamide chains therefore facilitates washing while at the same time decreasing the background noise during the subsequent detection, or even purely and simply elimination of the purification step.

According to a first embodiment of the invention, the latter proposes a temperature-stable labeling reagent of formula (0):

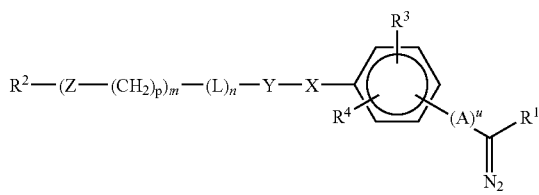

in which:
R¹ represents H or an alkyl, aryl or substituted aryl group,
R² represents a detectable marker or at least two detectable markers interlinked by at least one multimeric structure,
L is a linker arm comprising a linear chain of at least two covalent bonds and n is an integer equal to 0 or 1,
R³ and R⁴ represent, independently of one another: H, $NO_2$, Cl, Br, F, I, $R^2$-$(L)_n$-Y—X—, OR, SR, $NR_2$, R, NHCOR, CONHR, COOR, —CO—NH—$(CH_2)_3$—(O—$CH_2$—$CH_2$)$_3$—$CH_2$—NH—R, —CO—NH—$(CH_2)_3$—(O—$CH_2$—$CH_2$)$_4$—$CH_2$—NH—$R^2$ with R=alkyl or aryl,
A is a linker arm comprising at least one covalent double bond enabling the conjugation of the diazo function with the aromatic ring and u is an integer between 0 and 2, preferably 0 or 1,
—Y—X— represents —CONH—, —NHCO—, —$CH_2$O—, —$CH_2$S—,
—Z— represents —NH—, —NHCO—, —CONH— or —O—,
m is an integer between 1 and 10, preferably between 1 and 3, and
p is an integer between 1 and 10, preferably between 1 and 3.

According to a second embodiment of the invention, the latter relates to a labeling reagent, as claimed in claim 1, of formula (1):

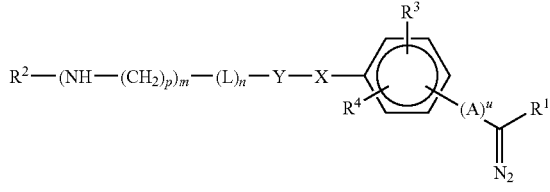

in which:
R¹ represents H or an alkyl, aryl or substituted aryl group,
R² represents a detectable label or at least two detectable labels interlinked by at least one multimeric structure,
L is a linker arm comprising a linear chain of at least two covalent bonds and n is an integer equal to 0 or 1,
R³ and R⁴ represent, independently of one another: H, $NO_2$, Cl, Br, F, I, $R^2$-$(L)_n$-Y—X—, OR, SR, $NR_2$, R, NHCOR, CONHR, COOR, —CO—NH—$(CH_2)_3$—(O—$CH_2$—$CH_2$)$_3$—$CH_2$—NH—$R^2$, —CO—NH—$(CH_2)_3$—(O—$CH_2$—$CH_2$)$_4$—$CH_2$—NH—$R^2$ with R=alkyl or aryl, and
—Y—X— represents —CONH—, —NHCO—, —$CH_2$O—, —$CH_2$S—,
m is an integer between 1 and 10, preferably between 1 and 3, and
p is an integer between 1 and 10, preferably between 1 and 3.

Advantageously, according to a variant of the first two embodiments, the value p is less than or equal to the value m in formula (0) or (1) of the reagent.

According to a third embodiment, the present invention proposes a reagent, as claimed in any one of claims 1 to 4, of formula (2):

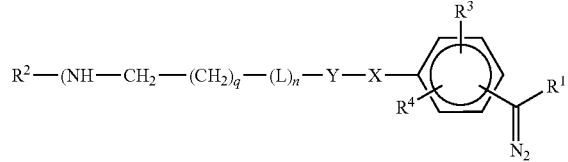

in which:
R¹ represents H or an alkyl, aryl or substituted aryl group,
R² represents a detectable label or at least two detectable labels interlinked by means of at least one multimeric structure,
L is a linker arm comprising a linear chain of at least two covalent bonds and n is an integer equal to 0 or 1,
R³ and R⁴ represent, independently of one another: H, $NO_2$, Cl, Br, F, I, $R^2$-$(L)_n$-Y—X—, OR, SR, $NR_2$, R, NHCOR, CONHR, COOR, —CO—NH—$(CH_2)_3$—(O—$CH_2$—$CH_2$)$_3$—$CH_2$—NH—$R^2$, —CO—NH—$(CH_2)_3$—(O—$CH_2$—$CH_2$)$_4$—$CH_2$—NH—$R^2$ with R=alkyl or aryl, and
q is an integer between 1 and 10, preferably between 1 and 3.

According to a fourth embodiment, the present invention describes a reagent, as claimed in any one of claims 1 to 4, of formula (3):

$R^2$—(NH—$CH_2$—$CH_2$)$_3$—NH—CO—$CH_2$—$CH_2$—CO—NH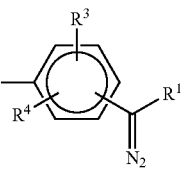

in which:
R¹ represents H or an alkyl, aryl or substituted aryl group,
R² represents a detectable label or at least two detectable labels interlinked by means of at least one multimeric structure, L is a linker arm comprising a linear chain of at least two covalent bonds and n is an integer equal to 0 or 1, and R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, —CO—NH—(CH$_2$)$_3$—(O—CH$_2$—CH$_2$)$_4$—CH$_2$—NH—R$^2$ with R=alkyl or aryl.

According to a variant associated with the fourth embodiment of the invention, R$^2$ consists of a D-biotin residue of formula (4):

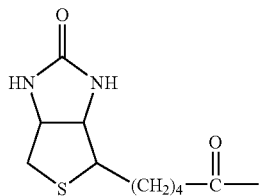

Advantageously, and whatever the embodiment previously mentioned for the reagent, R$^1$ consists of: CH$_3$, and R$^3$ and R$^4$ each represent: H.

Advantageously, and whatever the embodiment or variant previously mentioned for the reagent is, the structure -(L)$_n$- consists of:
spermine or N,N'-bis(3-aminopropyl)-1,4-diaminobutane: NH$_2$—(CH$_2$)$_3$—NH—(CH$_2$)$_4$—NH—(CH$_2$)$_3$—NH$_2$, or
spermidine or N-(3-aminopropyl)-1,4-butanediamine: H$_2$N—(CH$_2$)$_4$—NH—(CH$_2$)$_3$—NH$_2$, or
a derivative containing an alanine motif: NH$_2$—CH$_2$—CH$_2$—COOH.

According to a fifth embodiment of the invention, the latter also relates to a temperature-stable labeling reagent of formula (6):

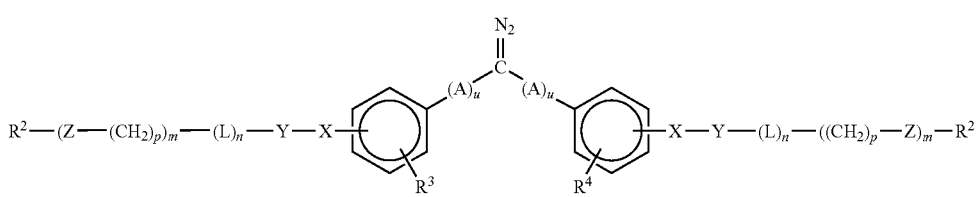

in which:
R$^1$ represents H or an alkyl, aryl or substituted aryl group,
R$^2$ represents a detectable label or at least two detectable labels interlinked by at least one multimeric structure, L is a linker arm comprising a linear chain of at least two covalent bonds and n is an integer equal to 0 or 1, R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, —CO—NH—(CH$_2$)$_3$—(O—CH$_2$—CH$_2$)$_4$—CH$_2$—NH—R$^2$ with R=alkyl or aryl, A is a linker arm comprising at least one covalent double bond enabling the conjugation of the diazo function with the aromatic ring and u is an integer between 0 and 2, preferably 0 or 1, —Y—X— represents —CONH—, —NHCO—, —CH$_2$O—, —CH$_2$S—, —Z— represents —NH—, —NHCO—, —CONH— or —O—, m is an integer between 1 and 10, preferably between 1 and 3, and p is an integer between 1 and 10, preferably between 1 and 3.

According to a sixth embodiment, the invention proposes a temperature-stable labeling reagent of formula (7):

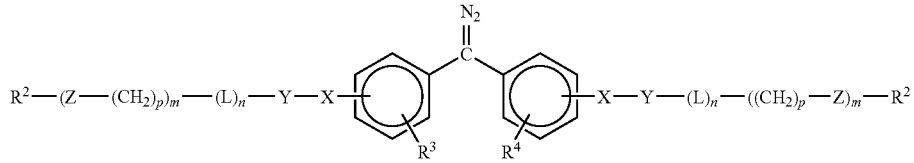

in which:
R$^1$ represents H or an alkyl, aryl or substituted aryl group,
R$^2$ represents a detectable label or at least two detectable labels interlinked by at least one multimeric structure, L is a linker arm comprising a linear chain of at least two covalent bonds and n is an integer equal to 0 or 1, R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, —CO—NH—(CH$_2$)$_3$—(O—CH$_2$—CH$_2$)$_4$—CH$_2$—NH—R$^2$ with R=alkyl or aryl, —Y—X— represents —CONH—, —NHCO—, —CH$_2$O—, —CH$_2$S—, —Z— represents —NH—, —NHCO—, —CONH— or —O—, m is an integer between 1 and 10, preferably between 1 and 3, and p is an integer between 1 and 10, preferably between 1 and 3.

Advantageously, and whatever the embodiment or variant previously mentioned for the reagent, L comprises a motif —(O—CH$_2$—CH$_2$)—, repeated from 1 to 20 times, preferably from 1 to 10 times, and even more preferably from 2 to 5 times, —Z— then being represented by —NH—, —NHCO— or —CONH—.

The invention also relates to a method for the synthesis of a labeling reagent, according to the above embodiments, comprising the following steps:

a) a label or a label precursor having a reactive function R$^6$ is provided,
b) a linker arm of formula (8):

is provided, in which formula:
- —Z— represents —NH—, —NHCO—, —CONH— or —O—,
- m is an integer between 1 and 10, preferably between 1 and 3,
- p is an integer between 1 and 10, preferably between 1 and 3,
- R$^7$ and R$^8$ represent two reactive functions which may be identical or different, c) the reactive function R$^6$ of said label or label precursor and the function R$^7$ of the linker arm of formula (8) are reacted together in the presence of at least one coupling agent so as to form a covalent bond, R$^6$ and R$^7$ being complementary,
d) a derivative of formula (9):

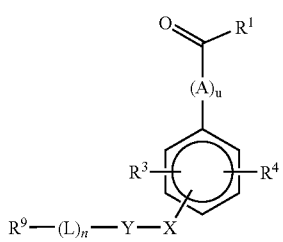

is provided, in which formula:
- R$^1$ represents H or an alkyl, aryl or substituted aryl group,
- L is a linker arm comprising a linear chain of at least two covalent bonds and n is an integer equal to 0 or 1,
- R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, —CO—NH—(CH$_2$)$_3$—(O—CH$_2$—CH$_2$)$_4$—CH$_2$—NH—R$^2$ with R=alkyl or aryl, —Y—X— represents —CONH—, —NHCO—, —CH$_2$O—, —CH$_2$S—, A is a linker arm comprising at least one covalent double bond enabling the conjugation of the diazomethyl function with the aromatic ring and u is an integer equal to 0 or 1, and R$^9$ represents a reactive function complementary to R$^8$, e) the reactive function R$^9$ of the derivative of formula (9) and the function R$^8$ of the linker arm of formula (8) are reacted together in the presence of at least one coupling agent so as to form a covalent bond,
f) the hydrazine or one of its derivatives is reacted with the ketone or aldehyde function so as to form a hydrazone, and
g) the hydrazone is converted to a diazomethyl function by means of an appropriate treatment.

Advantageously, the method of synthesis can also comprise:
- an additional step consisting of protection of the ketone or aldehyde function of compound (9), and
- a subsequent additional step consisting of deprotection of said ketone or aldehyde function.

The invention also relates to a method for the labeling of a biological molecule, in particular a nucleic acid, comprising bringing into contact, in homogeneous solution, in a substantially aqueous buffer, a biological molecule and a reagent, according to the embodiments mentioned above.

The invention also relates to a labeled biological molecule which can be obtained by means of the method, according to the labeling claim above.

The invention also relates to a method for the labeling and fragmentation of a single-stranded or double-stranded nucleic acid, comprising the following steps:
- fragmenting the nucleic acid,
- attaching a label to at least one of the fragments by means of a labeling reagent chosen from the reagents according to the embodiments mentioned above, said reagent coupling covalently and predominantly on at least one phosphate of said fragment.

Advantageously, the labeling and fragmentation method is carried out using a labeling reagent which is chosen from the compounds of formula (3):

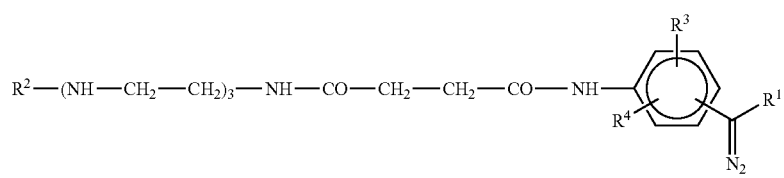

in which:
- R$^1$ represents H or an alkyl, aryl or substituted aryl group,
- R$^2$ represents a detectable label or at least two detectable labels interlinked by at least one multimeric structure,
- L is a linker arm comprising a linear chain of at least two covalent bonds and n is an integer equal to 0 or 1, and
- R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, —CO—NH—(CH$_2$)$_3$—(O—CH$_2$—CH$_2$)$_4$—CH$_2$—NH—R$^2$ with R=alkyl or aryl.

According to a first variant of implementation of the labeling and fragmentation method, the fragmentation and the labeling are carried out in two steps.

According to a second variant of implementation of the labeling and fragmentation method, the fragmentation and the labeling are carried out in one step.

Whatever the labeling and fragmentation method, the labeling is carried out in a substantially aqueous homogeneous solution.

Whatever the labeling and fragmentation method, the fragmentation is carried out via an enzymatic, physical or chemical process.

The present invention also relates to any labeled nucleic acid which can be obtained by means of the labeling and fragmentation method above.

The present invention also relates to a kit for the detection of a target nucleic acid, comprising a labeled nucleic acid as defined above.

The present invention always relates to a solid support to which is attached at least one reagent as defined above.

Finally, the present invention relates to a method for the capture of nucleic acids, comprising the following steps:
providing a solid support to which is directly or indirectly attached at least one biological molecule, defined above, or a nucleic acid, also defined above, the biological molecule or the nucleic acid comprising a diazomethyl function,
bringing into contact a biological sample which may contain free nucleic acids, and
washing the solid support where the molecule(s) is(are) covalently attached at least to one nucleic acid.

The term "multimeric structure" is intended to mean a polymer formed of repeat units of chemical or biological synthons. An example is mentioned in example 34.2 of the description of patent application WO-A-02/090319. Those skilled in the art are requested to refer to this document should they find the information developed hereinafter insufficient for their complete understanding of this subject. Many variants of such structures which can be used in the present invention are known, such as, for example:
linear polymers (EP-A-0.561.722, EP-A-0.669.991),
branched polymers (WO-A-01/92361),
particles (EP-A-0 827 552),
dendrimers (U.S. Pat. No. 4,507,466; U.S. Pat. No. 4,568,737; U.S. Pat. No. 6,083,708),
polynucleotides, and
polypeptides.

Should it prove necessary, those skilled in the art can also refer to these documents for a complete understanding of the subject.

The term "detectable label" is intended to mean at least one label capable of directly or indirectly generating a detectable signal. A nonlimiting list of these labels follows:
enzymes which produce a detectable signal, for example by colorimetry, fluorescence or luminescence, such as horseradish peroxidase, alkaline phosphatase, β-galactosidase or glucose-6-phosphate dehydrogenase,
chromophores, such as fluorescent, luminescent or dye compounds,
groups with an electron density detectable by electron microscopy or by virtue of their electrical property, such as conductivity, amperometry, voltammetry or impedance,
detectable group, for example the molecules of which are sufficiently large to induce detectable modifications of their physical and/or chemical characteristics; this detection can be carried out by optical methods such as diffraction, surface plasmon resonance, surface variation or contact angle variation, or physical methods such as atomic force spectroscopy or the tunnel effect,
radioactive molecules such as $^{32}P$, $^{35}S$ or $^{125}I$.

Preferably, the label is not a radioactive label, in order to avoid the safety problems associated with these labels.

In one specific embodiment of the present invention, the label is electrochemically detectable, and in particular the label is a derivative of an iron complex, such as ferrocene.

Indirect systems can also be used, such as, for example, ligands capable of reacting with an anti-ligand. The ligand/anti-ligand pairs are well known to those skilled in the art, which is the case, for example, of the following pairs: biotin-istreptavidin, hapten/antibody, antigen/antibody, peptide/antibody, sugar/lectin, polynucleotide/sequence complementary to the polynucleotide. In this case, it is the ligand which bears the diazomethyl reactive function. The anti-ligand can be directly detectable by means of the labels described in the above paragraph or can itself be detectable by means of another ligand/anti-ligand pair. This stacking system is illustrated in the examples.

Another example of indirect systems uses a specific covalent bond between the ligand and the anti-ligand, for example methyl ketone and alkoxyamine. Examples of this system are described in patent applications WO-A-00/40590 and WO-A-98/05766. These indirect detection systems can produce, under certain conditions, an amplification of the signal and reference may be made to the prior patent applications WO-A-00/07982, WO-A-01/92361 and WO-A-95/08000 for examples of chemical amplification using polymers, or to application WO-A-01/44506 for systems of chemical amplification by stacking.

In one specific embodiment of the signal amplification, at least two labels are present on the labeling reagent.

In one preferred embodiment of the invention, the tracer is a fluorescent compound with low steric hindrance, such as fluoresceine, hexachlorofluoresceine (HEX), dansyl (edans), rhodamine, tetramethylrhodamine (5- or 6-TAMRA), carboxy-X-rhodamine (ROX), chromophores of the NIR type (LI-COR Inc, Lincoln Nebr., USA), cyanine derivatives such as Cy5 and Cy3 (Randolph J. B. et al., Nucleic Acids Res., 25(14), p 2923-2929, 1997), and in particular Cy5 derivatives, or else the tracer is a hapten with low steric hindrance, such as biotin dinitrophenyl, or an abietane derivative (see application WO-A-00/07982). The term "low steric hindrance" is intended to mean a molecular weight of less than 1000 g/mol.

In the case of a fluorophore, it is preferable to work with fluorophores for which the excitation wavelength is greater than 450 nm, preferably greater than 600 nm.

When the tracer is a hapten which does not produce any signal by itself, for instance biotin, the detection is carried out by means of the recognition of a labeled anti-ligand as described above. In the case of biotin, use is preferably made of streptavidin or an anti-biotin antibody coupled to a fluorescent compound such as fluoresceine, Cy5 or phycoerythrin. In the case of abietane, a monoclonal antibody as described in patent application WO-A-00/07982 is used.

In particular, the labeling reagents of the invention are soluble in polar solvents such as DMF, DMSO, $CH_3CN$, THF, DMA (dimethylacetamide), NMP (N-methylpyrrolidone) or DME (dimethoxyethane).

The labeling reagents are preferably soluble in DMSO or water.

The term "water-miscible solvent" is intended to mean a solvent which is miscible in a proportion of at least 5% by volume with water or an aqueous buffer containing salts.

Advantageously, in the above formulae, the arm L comprises an ethylene glycol or polyethylene glycol motif in order to increase the water-solubility of the reagent.

A is a linker arm comprising at least one double bond of ethylenic type enabling the conjugation of the diazomethyl function with the aromatic ring. The function of the linker arm A is to distance the diazomethyl function from the ring in order to decrease the steric hindrance while at the same time conserving the stability of the diazomethyl function. The term "conjugation" is intended to mean electron delocalization of the aromatic ring along the carbon chain of the linker arm. By way of example, the arm A can have the following structure:

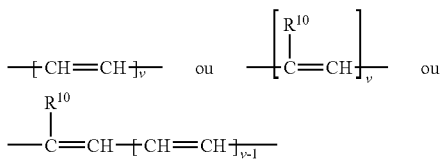

in which:
v is an integer of between 1 and 10, preferably v is 1 or 2, and
$R^{10}$ is H or an alkyl group, preferably $R^{10}$ is H, methyl or ethyl.

These reagents can thus attach in the homogeneous phase to the biological molecules, the homogeneous phase consisting of a substantially aqueous solution, i.e. a solution containing at least 50% of water.

The term "biological molecule" is intended to mean a compound which has at least one recognition site allowing it to react with a target molecule of biological interest. By way of example of biological molecules, mention may be made of nucleic acids, antigens, antibodies, polypeptides, proteins, haptens.

The term "nucleic acid" means a chain of at least two deoxyribonucleotides or ribonucleotides optionally comprising at least one modified nucleotide, for example at least one nucleotide comprising a modified base, such as inosine, methyl-5-deoxycytidine, dimethylamino-5-deoxyuridine, deoxyuridine, diamino-2,6-purine, bromo-5-deoxyuridine, or any other modified base allowing hybridization. This polynucleotide can also be modified at the level of the internucleotide bond, such as, for example, phosphorothioates, H-phosphonates or alkyl phosphonates, or at the level of the backbone, such as, for example, alpha-oligonucleotides (FR 2 607 507) or PNA (M. Eghohn et al., J. Am. Chem. Soc., 114, 1895-1897, 1992) or 2'-O-alkyl riboses. The nucleic acid can be natural or synthetic, an oligonucleotide, a polynucleotide, a nucleic acid fragment, a ribosomal RNA, a messenger RNA, a transfer RNA, or a nucleic acid obtained by means of an enzymatic amplification technique, such as:

PCR (Polymerase Chain Reaction), described in patents U.S. Pat. No. 4,683,195, U.S. Pat. No. 4,683,202 and U.S. Pat. No. 4,800,159, and its derivative RT-PCR (Reverse Transcription PCR), in particular in a one-step format, as described in patent EP-B-0.569.272, LCR (Ligase Chain Reaction), disclosed, for example, in patent application EP-A-0.201.184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, TMA (Transcription Mediated Amplification) with patent U.S. Pat. No. 5,399,491, and RCA (Rolling Circle Amplification (U.S. Pat. No. 6,576, 448).

The term "amplicons" is then used to denote the nucleic acids generated by an enzymatic amplification technique.

Each of these modifications can be taken in combination as long as at least one phosphate is present in the nucleic acid.

The term "polypeptide" is intended to mean a chain of at least two amino acids.

The term "amino acids" is intended to mean:
the primary amino acids which encode proteins,
the amino acids derived after enzymatic action, such as trans-4-hydroxyproline,
amino acids which are natural but are not present in proteins, such as norvaline, N-methyl-L leucine, staline (see Hunt S. in Chemistry and Biochemistry of the amino acids, Barett G. C., ed., Chapman and Hall, London, 1985), and
amino acids protected by chemical functions which can be used in solid-support or liquid-phase synthesis, and unnatural amino acids.

The term "hapten" denotes nonimmunogenic compounds, i.e. compounds incapable by themselves of promoting an immune reaction through the production of antibodies, but capable of being recognized by antibodies obtained by immunization of animals under known conditions, in particular by immunization with a hapten-protein conjugate. These compounds generally have a molecular mass of less than 3000 Da, and most commonly less than 2000 Da and may for example be glycosylated peptides, metabolites, vitamins, hormones, prostaglandins, toxins or various medicaments, nucleosides and nucleotides.

The term "antibody" includes polyclonal or monoclonal antibodies, antibodies obtained by genetic recombination, and antibody fragments such as Fab or F(ab')$_2$.

The term "antigen" denotes a compound capable of generating antibodies.

The term "protein" includes holoproteins and heteroproteins such as nucleoproteins, lipoproteins, phosphoproteins, metalloproteins and glycoproteins, both fibrous and globular in their characteristic conformational form.

Advantageously, the biological molecule has a phosphate group, i.e. a group having at least one motif:

which is either naturally present in the biological molecule, or can be introduced, for example, by chemical or enzymatic modification. Examples of chemical modification for proteins are given in "Chemistry of protein conjugation and cross linking", S. S. Wong, CRC Press, 1991.

Preferably, the biological molecule is a nucleic acid.

Certain advantageous reagents of the invention are:
a) of formula (10):

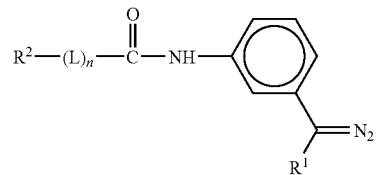

b) of formula (11):

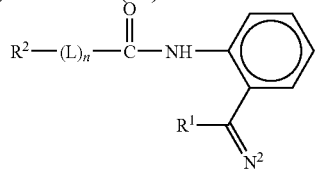

c) of formula (12):

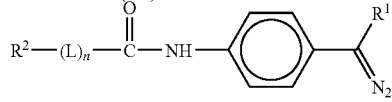

in which:

$R^1$ represents H or an alkyl, aryl or substituted aryl group, $R^2$ represents a detectable label or at least two detectable labels interconnected by at least one multimeric structure, L is a linker arm comprising a linear chain of at least two covalent bonds, and n is an integer equal to 0 or 1.

Preferably, the labeling reagent has the:

a) formula (13):

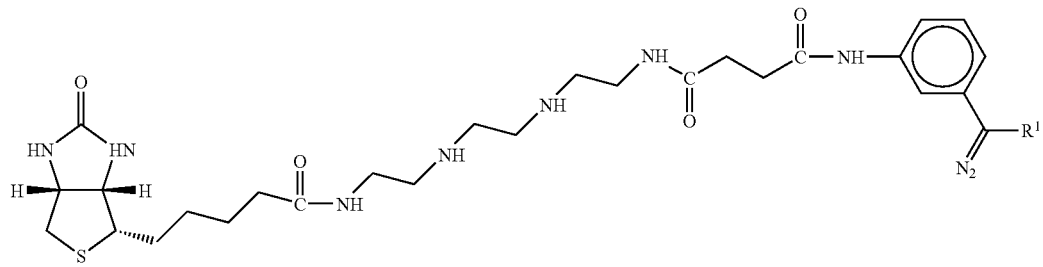

b) formula (14):

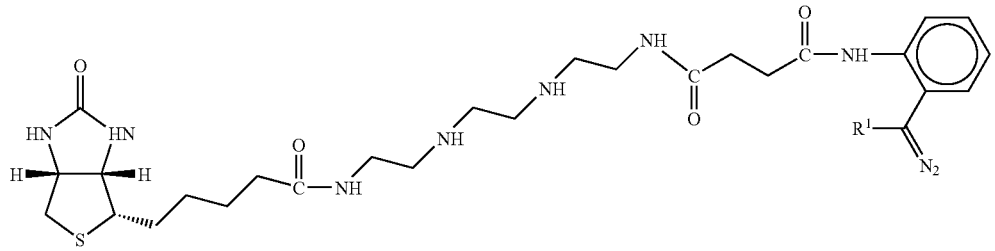

c) formula (15):

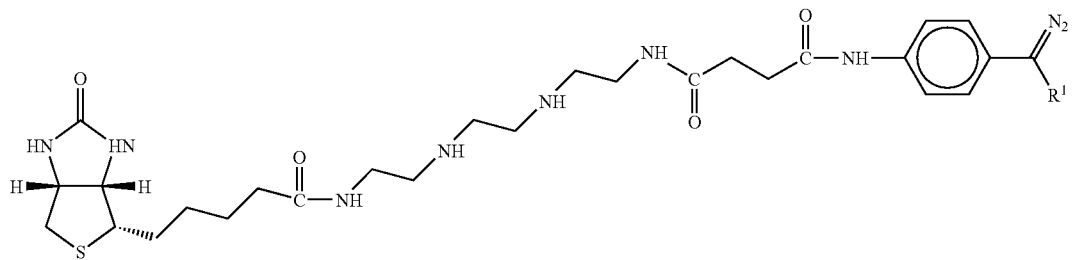

in which $R^1$ represents a methyl or phenyl group.

Whatever the variant and the embodiment of the reagent, L can comprise a motif —(NH—CH$_2$—CH$_2$)—, repeated from 1 to 20 times, preferably from 1 to 10 times, and even more preferably from 2 to 5 times.

The term "hydrazine derivative" is intended to mean a molecule having the NH$_2$—NH— function. Tosylhydrazine is an example of such a derivative.

The conversion of hydrazone to diazomethyl is carried out by the usual methods, in particular oxidation with MnO$_2$.

Other methods can be used, as described in X. Creary, Organic Syntheses, Wiley: New York, Coll. Vol. VII, p 438-443, 1990; H. Zollinger, Diazo Chemistry II, VCH, Weinheim, p 34-47, 1995; T. L. Holton and H. Shechter, J. Org. Chem., 60, 4725-4729, 1995.

In the case of the use of a tosylhydrazine derivative, the method is described in X. Creary, Organic Syntheses; Wiley: New York, Coll. Vol. VII, p 438-443, 1990.

In one specific embodiment of any one of the methods of synthesis, said method comprises:
an additional step consisting of protection of the ketone or aldehyde function (where R$^1$ is H) of compound (9), and
a subsequent additional step consisting of deprotection of said ketone or aldehyde function.

This protection is carried out by means of an acetal group, for example. The deprotection is carried out by an appropriate means, such as in an acidic medium for the acetal group. Those skilled in the art will determine, according to the compounds, at which step of synthesis these two protection and deprotection steps occur.

In the case of signal amplification, the method of synthesis is similar to those mentioned above. The label precursor can have formula (17) below

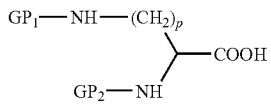

in which GP$_1$ and GP$_2$ represent two amine function-protecting groups, which may be identical or different, and p is an integer between 1 and 10, advantageously 2 and 6, preferably 4. Advantageously, GP$_1$ and GP$_2$ are different in order to be able to add several motifs, as explained below.

Examples of protective groups GP1 or GP2 which can be used in the present invention are given in T. W. Greene and P. G. M. Wuts, Protective Groups in Organic Synthesis, 2nd edition, John Wiley and Sons, New York, 1991, preferably those commonly used in peptide synthesis, such as Boc (tert-butyloxycarbonyl), Fmoc (9-fluorenylmethyleneoxycarbonyl), Cbz (carboxybenzyl) or Alloc (allyloxycarbonyl).

In particular, GP1 and GP2 are, respectively, the protective groups Boc and Fmoc.

The reaction between this precursor which has a carboxyl function and the derivative of formula (18), hereinafter, is carried out in the presence of a coupling agent so as to form the amide bond.

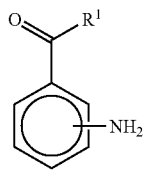

After deprotection, under usual conditions, of one of the two protective groups, for example Fmoc, with a base such as piperidine, the freed amine function is used to couple another molecule of formula (17). This process is repeated as many times as necessary to obtain a multitide of NH$_2$ functions protected with a protective group, for example a Boc function. The motif is added between one (1) and a hundred (100) times, preferably between one (1) and twenty (20) times.

Hydrazine is reacted with the ketone function originating from the phenyl ketone derivative so as to form a hydrazone, and then oxidation is carried out in the presence of MnO$_2$ so as to form a diazomethyl residue. Then, after deprotection of the amine function bearing the Boc group, a tracer, for example a biotin activated with an N-hydroxysuccinimide group, is coupled to the amine functions so as to produce a reagent in which the motif R$^2$-(L)$_n$- is that of formula (5).

Another object of the present invention is to describe a method, and also the products obtained by means of this method, for the labeling of a biological molecule, in particular a nucleic acid, comprising bringing into contact in solution, in a substantially aqueous homogeneous solution, a biological molecule and a labeling reagent according to the invention.

The term "substantially aqueous solution", is intended to mean a solution containing at least 50% of water. This solution preferably contains salts, such as a buffer solution.

The term "homogeneous solution" is intended to mean a single-phase solution such as a water/DMSO solution, as opposed to a two-phase solution such as a water/chloroform solution.

The specific conditions for the labeling reactions vary according to the biological molecules and to the label. As regards nucleic acids, a pH of between 5 and 8 allows efficient labeling. In particular, a pH of between 5.5 and 7.0 is preferred for all the reagents of the invention. With the reagent of formula (11), the pH range is broader for the labeling. Good labeling efficiency is obtained for a pH of between 3 and 8 for this reagent.

This labeling and fragmentation method is particularly useful when the labeled nucleic acid must hybridize with a multitude of nucleic acids, in particular oligonucleotides, attached to the solid support at a predetermined position so as to form a DNA chip. The term "DNA chip" is intended to mean a solid support of small size, to which is attached a multitude of capture probes at predetermined positions. Specifically, the density of the nucleic acids attached to the solid support imposes considerable steric constraints during hybridization and fragmentation makes it possible to improve this hybridization step. Examples of these DNA chips are given, for example, in the publications by G. Ramsay, Nature Biotechnology, 16, p 40-44, 1998; F. Ginot, Human Mutation, 10, p 1-10, 1997; J. Cheng et aL, Molecular diagnosis, 1(3), p 183-200, 1996; T. Livache et al., Nucleic Acids Research, 22(15), p 2915-2921, 1994; J. Cheng et al., Nature Biotechnology, 16, p 541-546, 1998.

The fragmentation and the labeling are carried out in one step or in two steps and the labeling can be carried out, without distinction, before, after or simultaneously with the fragmentation.

Preferably, the labeling and fragmentation are carried out simultaneously, i.e. the reagents required for these two steps are placed together in a substantially aqueous homogeneous solution with the nucleic acid, for example. This is in particular the case for chemical or enzymatic fragmentation. In the case of mechanical fragmentation by a physical means, "labeling and fragmentation being carried out simultaneously" signifies that the physical means is applied to a substantially aqueous homogeneous solution containing at least the nucleic acids and the labeling reagent.

The fragmentation of the nucleic acid is carried out by an enzymatic, chemical or physical process.

The fragmentation of the nucleic acid by an enzymatic process is carried out, for example, with nucleases.

The fragmentation of the nucleic acid by a physical process is carried out, for example, by sonication or by radiation.

The fragmentation by a chemical process, if the nucleic acid is an RNA, is carried out by the usual methods (see, for example, Chem. Rev, 98, 961-990, 1998 by Oivanen M. et al.).

Metal complexes, as described in the review by G. Pratviel et al., Adv. Org. Chem., 45, p 251-312, 1998 or the review by G. Pratviel et al., Angew. Chem. Int. Ed. Engl., 34, p 746-769, 1995, can be used for the fragmentation of DNA or RNA.

In a first embodiment, the chemical fragmentation of RNA is carried out with metal cations possibly associated with a chemical catalyst. In this case, the metal cations are $Mg^{2+}$, $Sr^{2+}$, $Ba^{2+}$, $Pb^{2+}$, $Zn^{2+}$, $Cd^{2+}$, $Mn^{2+}$, $Fe^{2+}$, $Co^{2+}$, $Ni^{2+}$, $Ru^{3+}$, $Ce^{3+}$, $Eu^{3+}$, $Tb^{3+}$, $Tm^{3+}$, $Yb^{3+}$ or $Lu^{3+}$ ions, the chemical catalyst consists of imidazole, a substituted analog, for example, N-methyl-imidazole, or any chemical molecule having an affinity for RNA and bearing an imidazole ring or a substituted analog. The conditions for fragmentation using metals are well described in patent application WO-A-99/65926. Advantageously, the metals are $Mg^{2+}$, $Mn^{2+}$, $Zn^{2+}$, $Tb^{3+}$ or $Ce^{3+}$, preferably $Mg^{2+}$, $Mn^{2+}$, $Zn^{2+}$.

Efficient fragmentation conditions are obtained with a concentration of metal cation such as $Mn^{++}$ of between 2 and 100 mM, and a concentration of imidazole of between 2 and 100 mM.

Especially efficient conditions are obtained with a concentration of cation such as $Mn^{++}$ of between 3 and 15 mM, and a concentration of imidazole of between 20 and 50 mM, in particular 30 mM.

The pH of the reaction must be slightly basic. Advantageously, the pH is between 8.5 and 9, which represents a very advantageous compromise for carrying out the labeling and fragmentation combination with RNA.

In a second embodiment, the chemical fragmentation of RNA is carried out by the action of a polyamine, such as spermine, putrescine or cadaverine. Concentrations of 5 to 100 mM allow fragmentation. The latter is complete starting from 10 mM of polyamine.

In a third embodiment, the chemical fragmentation of RNA is carried out by the action of an artificial nuclease (see G. Pratviel et al., Adv. Inorg. Chem., 45, p 251-312, 1998; D. S. Sigman et al. Chem. Rev., 93, p 2295-2316, 1993), such as 1,10-phenanthroline associated with a metal cation such as iron, copper or zinc. These cations originate, respectively, from $FeSO_4$, $CuCl_2$ or $ZnCl_2$ in solution. Concentrations of between 2 and 50 mM of 1,10-phenanthroline are used for RNA fragmentation, in particular of between 4 and 10 mM.

The fragmentation of DNA by a chemical process is carried out by bringing the nucleic acid together with a chemical means of creating an a basic site. The formation of an abasic site results from cleavage of the N-glycoside bond which links the 2-deoxyribose sugar to the nucleic base. This involves a depurination via the loss of a negatively charged purine (guanine, adenine), or a depyrimidination in the case of the loss of a pyrimidine (cytosine, thymine), which is positively charged.

This depurination is spontaneous under physiological conditions (pH 7.4 at 37° C.), but the reaction rate is very low, of the order of $3 \times 10^{11}$ depurination per second, i.e. unusable for efficient fragmentation. In order to increase the reaction rate, alkylating agents which make the N-glycoside bond fragile are used or uracil-DNA glycosylases are used on DNAs which incorporate uracils.

The abasic site obtained by depurination or depyrimidation is very unstable. The fragmentation at this site is obtained at ambient temperature in a basic medium. In acidic medium, high temperature also accelerates this fragmentation. The use of molecules capable of initiating the β-elimination phenomenon also accelerates fragmentation.

A preferred embodiment of the fragmentation is obtained by using an acidic pH, i.e. a pH of less than 5. Advantageously, the pH is 3.

A sodium formate buffer at pH 3 makes it possible to efficiently fragment according to the invention. This buffer is compatible with the conditions for one-step labeling as will be demonstrated in the examples. Even more advantageously, an acidic medium (HCl, carbonate, $H_2SO_4$) is used.

In one specific embodiment of the present invention, and with the aim of further increasing the fragmentation, the deoxyribonucleic acid contains at least one modified base capable of generating an abasic site more readily.

Various modified bases can be used, such as N7-alkyl purines, N3-alkyl purines, O6-alkyl purines, 8-bromopurines, 8-thiopurines, 8-alkylthiopurines, 8-azidopurines or 8-alkylsulfonylpurines.

When the nucleic acid to be labeled is generated by an enzymatic amplification technique such as PCR, the use of an 8-bromopurine makes it possible to have efficient incorporation during the amplification, which facilitates accordingly the fragmentation and labeling method according to the invention, while at the same time conserving excellent sensitivity for the enzymatic amplification step.

The present invention describes a labeled biological molecule, and in particular a labeled nucleic acid, which can be obtained by means of any one of the methods according to the invention.

The present invention also relates to a kit for the detection of a biological molecule, in particular a target nucleic acid, comprising a labeling reagent according to the invention. Depending on the uses of the kit, other elements, such as, for example lysis means (microorganisms and/or cells) and/or concentration means (such as silica or magnetic particles) and/or enzymatic amplification means are incorporated into the kit.

The invention relates to the use of a labeled biological molecule, in particular a labeled nucleic acid as defined above, as a probe for the detection of a target biological molecule, and in particular of a target nucleic acid.

The invention also relates to the use of a nucleic acid as defined above, as a labeled target which can attach to a capture probe.

In order to allow the detection and/or the quantification and/or the purification of the target biological molecule, the labeled biological molecule is capable of forming a complex with the target biological molecule. By way of example, for demonstrating a target molecule of nucleic acid type, the labeled nucleic acid is sufficiently complementary to the target to hybridize specifically according to the reaction conditions, and in particular the conditions of temperature or of salinity of the reaction medium.

The detection method is applicable for sequencing, the expression profile of messenger RNAs or the screening of mutations for research purposes and also the screening of drugs in the pharmaceutical industry, the diagnosis of infectious or genetic diseases, or food product or industrial controls.

The tendency in terms of diagnosis, and in particular for infectious diseases (AIDS or tuberculosis, for example), is to reduce the level of sensitivity, until a single molecule is detected in a sample, which can represent several milliliters in the case of a liquid sample such as blood, urine or cerebralspinal fluid. This level of sensitivity can also be obtained if all the steps from the taking of the sample to the delivery of the result, are optimized. The various means of the invention allow this optimization without difficulty because the reagents, methods and methods of the invention are very broadly applicable to various biological molecules. In particular, when an enzymatic amplification step is necessary in order to obtain the required sensitivity (viral or bacterial infection such as HIV, HCV or tuberculosis), a labeling and/or fragmentation method, as described in the present invention, makes it possible not to affect the sensitivity of the amplification technique, either because it is not necessary to replace the deoxyribonucleotides or the ribonucleotides used in the enzymatic amplification technique, or because the ribonucleotides or deoxyribonucleotides incorporated do not impair the sensitivity.

The grafting chemistry described in the present invention has characteristics such, from the reactivity and specificity point of view, that other applications are described hereinafter:

In a first embodiment, this grafting chemistry is applied to the covalent attachment of nucleic acids to a solid support.

In a first variant of the method, a precursor of the diazomethyl function, such as a ketone or a hydrazine as described above, is introduced during the chemical synthesis and the diazomethyl function is introduced onto the nucleic acids in a second step.

In a second preferred variant of the method, the diazomethyl functions are introduced onto the solid support and the nucleic acids are attached to the solid support by means of the phosphates of the nucleic acids, and in particular of the end (5' or 3') phosphates.

The introduction of phosphate at the 3' or 5' end of nucleic acids is known (see "Protocols for Oligonucleotides and Analogs, Synthesis and Properties" edited by S. Agrawal, Humana Press, Totowa, N.J.).

In one specific embodiment of such a solid support, a labeling reagent bearing a ligand, in particular a hapten such as biotin or abietane, is attached to the solid support to which an anti-ligand, such as streptavidin or an antibody, for example, is attached covalently or by adsorption. These solid supports are well known in the prior art and are even commercially available (microtitration plate-streptavidin or latex-streptavidin, for example). The function of the label is no longer, in this case, to allow detection, but to allow attachment of the labeling reagent to the solid support. The diazomethyl function is then available to react with nucleic acids. The derivatives of formulae (13), (14) and (15) or the PDAM derivative are examples of reagents which can be used for the fabrication of such a solid support. The monoclonal antibody technique makes it possible to prepare antibodies against a large number of labels such as fluorescein or a Cy5 derivative. Those skilled in the art can use a solid support with the labeling reagents of the present invention without excessive difficulty through this method of indirect preparation of the solid support in which a ligand/anti-ligand reaction is used to attach the diazomethyl function to the solid support.

A second embodiment of the solid support concerns particulate supports such as latexes. Various methods of polymerization can be used to prepare the particles bearing a diazomethyl function from a polymerizable functional monomer bearing either a diazomethyl function or preferably a precursor function of the diazomethyl function, such as an aldehyde or a ketone, and in particular:

Closed-reactor polymerization termed "batch": the monomers are introduced into the reactor, before the beginning of the reaction, with the other ingredients and without subsequent addition. Because of the difference in reactivity of the monomers, this method often leads to the appearance of a drift in composition. This manifests itself through the production of macromolecules having compositions which vary considerably as a function of the conversion. This method is relatively inefficient for surface incorporation, since there is a risk of a considerable portion of the functional monomer being lost either inside the particles, or in the form of water-soluble polymer. When the copolymerization is performed by "batch" with monomers of a polar nature, smaller particles are obtained, in large number, but with a limited conversion. This behavior is linked to the considerable water-solubility of these monomers, and it is attributed to the predominance of the homogeneous nucleation mechanism.

Semicontinuous polymerization: a portion at least of the monomers is introduced into the reactor over a period between the start of the reaction and the end of the latter. This addition can be carried out at a fixed rate or else following a given profile. The aim is to control the addition of the monomer mixture in such a way as to obtain a copolymer of controlled composition (control of the composition of the interface); thus, addition conditions are often obtained such that the rate of polymerization is faster than the rate of addition.

Polymerization by deferred addition termed "shot": once the polymerization reaction is in progress, the functional monomer alone, or in the presence of the basic monomer, is introduced into the system in a controlled manner. The success of the process therefore depends on the degree of prior knowledge of the kinetics of copolymerization. It is an efficient method for promoting surface incorporation. The selection of the experimental conditions (degree of conversion at the time of addition, composition and concentration of the monomer mixture) makes it possible to optimize the surface yields.

Seed polymerization: it consists in introducing the functional monomer into the system containing a latex which is already constituted and completely characterized. The functional monomer can be added alone or as a mixture with the basic monomer of the seed, in one step or semicontinuously.

The seed polymerization, shot polymerization and semicontinuous polymerization techniques are preferred since they result in a maximum of incorporation of the derivative bearing the precursor of the diazomethyl function at the surface. Examples of particles bearing aldehyde functions are given, for example, in B. Charleux et aL, Die Makromolecular Chem., 193, p 187 and p. 205, 1992, or in patent EP-B-0.350.407.

A third embodiment of the solid support consists in providing a solid support comprising a first nucleophilic or electrophilic reactive function, such as, for example, $NH_2$, SH, OH, O—$NH_2$, alkyl ketone, aldehyde, isocyanate, isothiocyanate, maleimide, alkyl halide, N-hydroxysuccinimide ester, or tosylate, and then in reacting an attachment intermediate, comprising a reactive function complementary to the first reactive function of the solid support. This reaction between the solid support and the attachment intermediate is carried out in the presence, optionally, of a coupling agent so as to form a covalent bond.

Such a solid support comprising at least one diazomethyl function, according to the various embodiments described above, in particular a solid support to which is indirectly attached a labeling reagent of the invention, is also a subject of the present invention, as is the solid support comprising nucleic acids attached to the solid support by means of the diazomethyl functions.

A first application of such a solid support is the fabrication of DNA chips. Methods exist for distributing nucleic acids on the solid support in discrete and predetermined positions.

U.S. Pat. No. 6,110,426 proposes a method for producing these DNA chips using a capillary, which is brought into contact on a solid surface so as to deliver a controlled volume of liquid. An effective contact takes place between the end of the capillary and the solid support so that the drop is deposited by capillary action. Similarly, U.S. Pat. No. 6,083,763 describes a set of capillaries which slide in a device so as to compensate for the differences in height of each of them. They are brought into contact with a planar surface for the deposition, by capillary action, of specific oligonucleotides.

U.S. Pat. No. 6,083,762 proposes a drop distribution system comprising a microdispenser coupled to a piezoelectric transducer for ejecting drop volumes of less than a nanoliter onto a solid surface. A similar result is obtained by applying a hot source to the wall of a capillary so as to form a bubble which ejects a defined volume of solution (see T. Okamoto et al., Nature Biotechnology, 18, p 438-441, 2000).

The diazomethyl function thus makes it possible to covalently graft the nucleic acids onto the support. The grafting is simple, the bonding is stable, compared with adsorption in particular, and the selectivity of the reaction with respect to the end phosphate makes it possible to perform an oriented coupling of the nucleic acid on the solid support, which facilitates accordingly the subsequent hybridization steps by decreasing the steric hindrance.

A second application of a solid support according to the invention is the purification of nucleic acids.

In the case of purification, this purification is either direct (the solid support bearing diazomethyl functions reacts with the nucleic acids to be purified) or indirect (capture nucleic acids are attached to the solid support). These capture nucleic acids are sufficiently complementary to the target to be captured so that they hybridize with the desired degree of specificity, and it is the "capture nucleic acids/solid support" complex which enables the purification of the target nucleic acids.

The solid support is preferably dispersed for the use in purification, such as latex particles, for example magnetic particles.

The term "purification step" is intended in particular to mean the separation of the nucleic acids from the microorganisms and the cellular constituents released in the lysis step which precedes the nucleic acid purification. These lysis steps are well known; as an example by way of indication, use may be made of the lysis methods as described in patent applications:

WO-A-00/60049 regarding lysis by sonication,
WO-A-00/05338 regarding mixed magnetic and mechanical lysis,
WO-A-99/53304 regarding electrical lysis, and
WO-A-99/15621 regarding mechanical lysis.

Those skilled in the art may use other well known lysis methods, such as heat shock or osmotic shock, or treatments with chaotropic agents, such as guanidium salts (U.S. Pat. No. 5,234,809).

This step generally makes it possible to concentrate the nucleic acids. By way of example, use may be made of magnetic particles (in this respect see U.S. Pat. No. 4,672,040 and U.S. Pat. No. 5,750,338), and it is thus possible to purify the nucleic acids, which have attached to these magnetic particles, by means of a washing step. This nucleic acid purification step is particularly advantageous if it is desired to subsequently amplify said nucleic acids. A particularly advantageous embodiment of these magnetic particles is described in patent applications WO-A-97/45202 and WO-A-99/35500.

The term "solid support" as used here includes all materials to which a nucleic acid can be attached. Synthetic materials or natural materials, optionally chemically modified, can be used as a solid support, in particular polysaccharides, such as cellulose-based materials, for example paper, cellulose derivatives such as cellulose acetate or nitrocellulose, or dextran; polymers, copolymers, in particular based on styrene-type monomers, natural fibers such as cotton, and synthetic fibers such as nylon; mineral materials such as silica, quartz, glasses, ceramics; latexes; magnetic particles; metal derivatives, gels, etc. The solid support can be in the form of a microtitration plate, of a membrane, of a particle or of a substantially planar glass or silicon plate, or derivatives.

Finally, the invention relates to a method for the capture of nucleic acids, comprising the following steps:
providing a solid support to which is directly or indirectly attached at least one molecule comprising a diazomethyl function,
bringing into contact a biological sample which may contain free nucleic acids, and
washing the solid support where the molecule(s) is (are) covalently attached at least to a nucleic acid.

Additional information can be found in another patent application by the Applicant, WO02/090584, filed under the priority of May 4, 2001.

The attached examples and figures represent specific embodiments and cannot be considered to limit the scope of the present invention.

EXAMPLE 1

Synthesis of the Reference Reagent: meta-BioPMDAM

Figure 1:
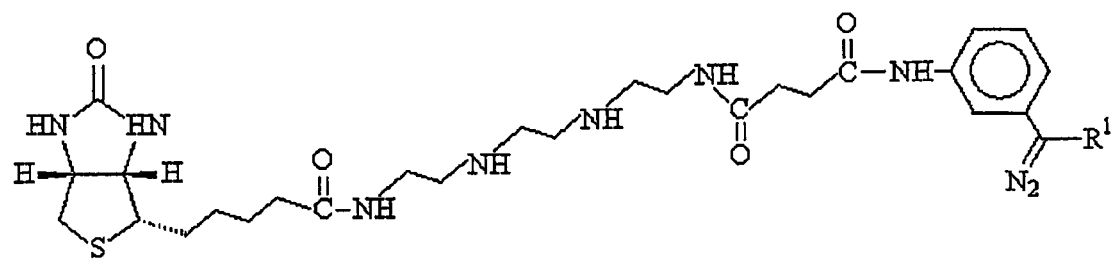
FIG. 1 represents the structural formulae of various reagents used in the present invention and also the abbreviation denoting them (o- signifies ortho, m- meta and p- para).
Figure 1:
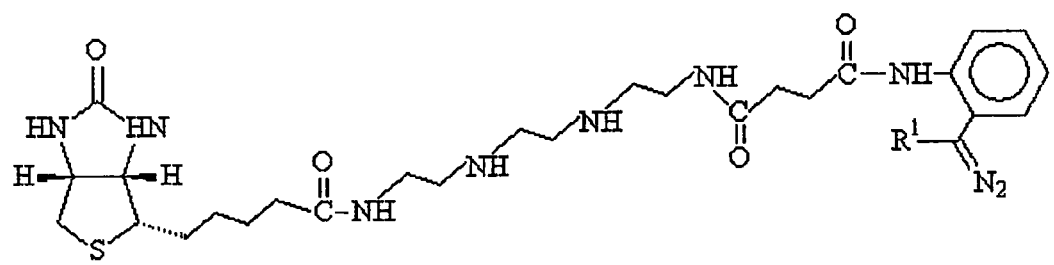
Figure 1:
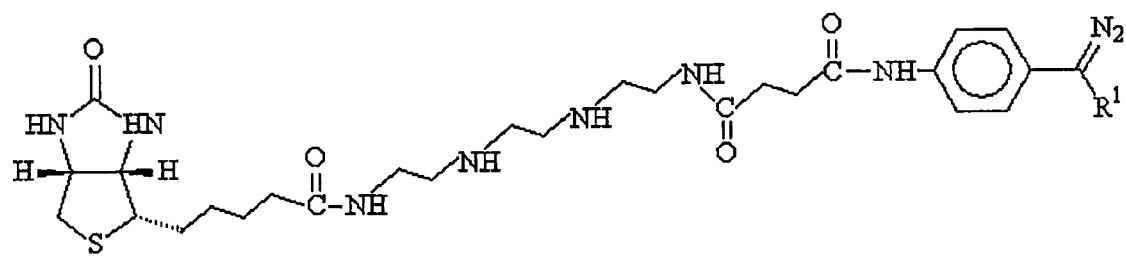
Figure 2:
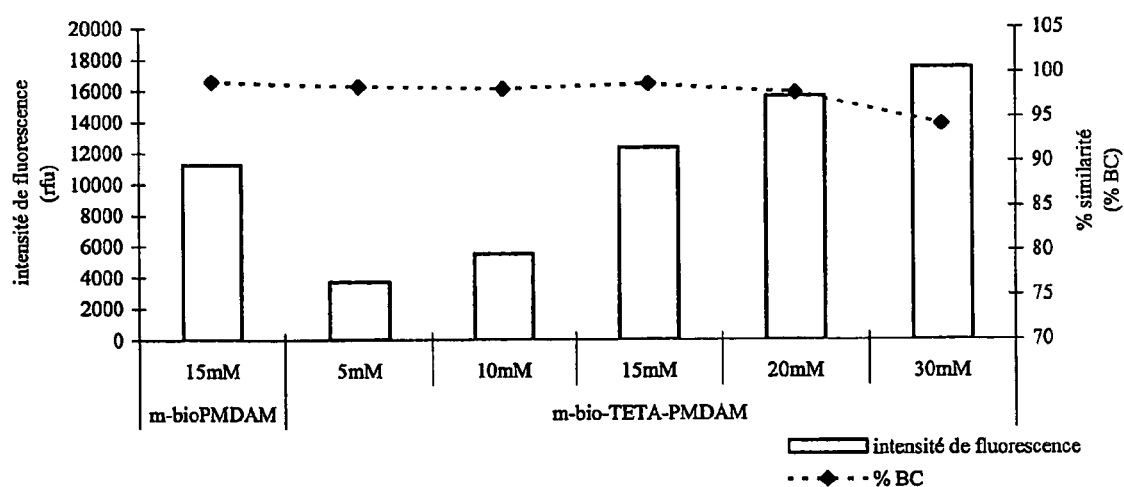
FIG. 2 represents the average value of the signal and the percentage similarity of m-bio-TETA-PMDAM as a function of its concentration for rpoB.

Biotin Meta-acetophenone Compound 1a:

D-Biotin (1.0 gram (g), 4.1 millimol (mmol)) is solubilized in 45 milliliters (ml) of anhydrous DMF under hot conditions. The product is cooled to 0° C. under argon, and then N-methylmorpholine (590 microliters (μl), 5.33 mmol) and isobutyl chloroformate (840 μl, 6.60 mmol) are added successively. The mixture is left to stir for 30 minutes (min), and then 3-aminoacetophenone (824 mg, 6.10 mmol) and N-methylmorpholine (480 μl, 4.35 mmol) in 10 ml of DMF are added. The solution is kept stirring at 0° C. for 2 hours (h), and then evaporated to dryness. The residue is taken up in 3 ml of MeOH, and then 50 ml of water are added. The precipitate obtained is filtered off, and washed with water, $CH_2Cl_2$ and ether, to give 1.2 g (80%) of crude product 1a. Recrystallization from the couple MeOH—$H_2O$ gives 1a (1.01 g, 70%) in the form of a white powder.

Mp 145° C.-IR (KBr): 3280, 2931, 2857, 1691, 1590, 1540, 1487, 1434, 1298, 1266 cm$^{-1}$. $^1H$ NMR (300 MHz, DMSO-$d_6$) δ=1.3-1.7 (m, 6H); 2.33 (t, J=8 Hz, 2H); 2.55 (s, 3H); 2.58; (d, J=12 Hz, 1H); 2.83 (dd, J=12 and 5 Hz, 1H); 3.13 (m, 1H); 4.15 (m, 1H); 4.31 (m, 1H); 6.34 (s, 1H); 6.41 (s, 1H); 7.44 (t, J=8 Hz, 1H); 7.64 (d, J=8 Hz, 1H); 7.85 (d, J=8 Hz, 1H); 8.17 (s, 1H); 10.05 (s, 1H).-MS (FAB/glycerol), m/z: 362 [M+H]$^+$.

Meta-Hydrazone Compound 2a:

A solution of 1a (500 mg, 1.38 mmol) and of hydrazine monohydrate (200 μl, 4.15 mmol) in absolute ethanol (8 ml) is refluxed for 2 h. After cooling to ambient temperature, the white precipitate is filtered off, washed with water and then with ether, and dried. 385 mg (74%) of product 2a are thus obtained in the form of a white powder.

Mp 185° C.-IR (KBr): 3298, 2931, 2857, 1698, 1665, 1626, 1541, 1494, 1470, 1446, 1330, 1265 cm$^{-1}$. $^1$H NMR (300 MHz, DMSO-$d_6$) δ=1.3-1.7 (m, 6H); 1.98 (s, 3H); 2.26 (t, J=8 Hz, 2H); 2.56 (d, J=12 Hz, 1H); 2.81 (dd, J=12 and 5 Hz, 1H); 3.11 (m, 1H); 4.13 (m, 1H); 4.29 (m, 1H); 6.39 (s, 3H); 6.42 (s, 1H); 7.22 (m, 2H); 7.50 (d, J=8 Hz, 1H) 7.84 (s, 1H); 9.82 (s, 1H).-MS (FAB/glycerol), m/z: 376 [M+H]

Meta-Diazomethane Compound 3a:

2a (180 mg, 0.48 mmol) is solubilized in 2 ml of DMF. $MnO_2$ (340 mg, 3.9 mmol) is then added. After stirring for 30 minutes at normal temperature, the mixture is filtered through a sintered glass funnel containing celite (thickness: 0.5 cm) and powdered 3 Å molecular sieves (0.5 cm). The reaction mixture is concentrated to a volume of approximately 0.5 ml, and then 5 ml of ether are added. The resulting precipitate is filtered off, washed with ether, and then dried. Compound 3a (170 mg, 95%) is obtained in the form of a pink powder.

Mp 160° C.-IR (KBr): 3278, 2935, 2859, 2038, 1704, 1666, 1605, 1577, 1536, 1458, 1430, 1263 $cm^{-1}$.-$^1$H NMR (300 MHz) δ=1.3-1.7 (m, 6H); 2.11 (s, 3H); 2.28 (t, J=8 Hz, 2H); 2.57; (d, J=12 Hz, 1H); 2.81 (dd, J=12 and 5 Hz, 1H); 3.11 (m, 1H); 4.13 (m, 1H); 4.29 (m, 1H); 6.33 (s, 1H); 6.41 (s, 1H); 6.60 (m, 1H); 7.25 (m, 3H); 9.84 (s, 1H)).

EXAMPLE 2

Synthesis of the Reagent
N-(3,6,9-triaminenonanyl)-biotinamide (Bio-TETA) (1)

D-Biotin (2.80 g, 11.40 mmol) is dissolved in 30 ml of anhydrous DMF. The addition of carbonyldiimidazole (1.5 eq.; 2.78 g) brings about, after a few minutes, the formation of a precipitate. After activation for 30 min, the resulting suspension is carefully added to triethylenetetramine (2 eq.; 5.00 g) in suspension in 20 ml of DMF. The reaction is left for 2 h on an oil bath at 60° C.

The product is purified by flash chromatography on silica gel, with 20:80:3 $CH_2Cl_2$/MeOH/$NH_4OH$ as eluent. After evaporation of the fractions concerned, 1.94 g of product are obtained in the form of a white powder (46%).

$^1$H NMR (200 MHz, DMSO-$d_6$) δ=7.75 (s, 1H, —NH—CO—); 6.40 (d, 2H, —NH— biot); 4.30 (t, 1H, —CH— biot); 4.15 (d, 1H, —CH— biot); 3.30 (m, 12H, —CH—NH—); 3.11 (m, 1H, —CH—S—); 2.8 (dd, 2H, —$CH_2$—S—); 2.55 (m, 5H, —NH—$CH_2$— & —$NH_2$); 2.04 (t, 2H, —$CH_2$—CO—); 1.52 (m, 6H, —$CH_2$—).

N-(3'-Acetophenyl) succinamic acid (ACBA) (2)

3-Aminoacetophenone (5.0 g; 37 mmol) is dissolved in 50 ml of anhydrous acetonitrile under argon. Succinic anhydride (1.3 eq.; 4.62 g) is added and allowed to react for one hour under argon. Product 2 appears in the form of a precipitate. After filtration and washing of the precipitate with ether, 7.29 g of white powder are obtained (84%).

$^1$H NMR (200 MHz, DMSO-$d_6$) δ=12.10 (s, 1H, —OH); 10.17 (s, 1H, —NH—); 8.19 (s, 1H); 7.82 (d, 1H); 7.66 (d, 1H); 7.50 (t, 1H); 2.56 (m, 7H, —$(CH_2)_2$— and —$CH_3$).

N-(3'-Acetophenyl)-N'-(3,6-diamine-9-biotinoylaminononanyl)succinamide (Bio-(TETA)-AP) (3)

The ACBA (2) (1.03 g; 4.39 mmol) is dissolved in 20 ml of anhydrous DMF under argon. The medium is cooled in ice, and N-methylmorpholine (1.25 eq.; 725 µl) and isobutyl chloroformate (1 eq.; 690 µl) are added successively; the medium becomes cloudy after 30 min. In parallel, the Bio-TETA (1) (0.8 eq.; 1.94 g) is solubilized under hot conditions in 50 ml of DMF and of triethylamine (0.8 eq.; 750 µl). It is added to the activated ACBA at 0° C., for 30 min. The mixture is then left at ambient temperature overnight. The purification is carried out by flash chromatography on silica gel, with 85:30:3 $CH_2Cl_2$/MeOH/$NH_4OH$ as eluent. The fractions containing product 3 are combined and the solvent is evaporated off. 1.01 g of white solid is obtained in the form of flakes (33%).

$^1$H NMR (200 MHz, DMSO-$d_6$) δ=10.16 (s, 1H, Ph-NH—CO—); 8.18 (s, 1H); 7.97 (s, 1H, —CO—NH—$CH_2$—); 7.80 (d, 1H); 7.85 (s, 1H, —$CH_2$—NH—CO—); 7.60 (d, 1H); 7.43 (t, 1H); 6.38 (d, 2H, —NH— biot); 4.3 (t, 1H, —CH— biot); 4.10 (d, 1H, —CH— biot); 3.35 (m, 12H, —CH—NH—); 3.10 (m, 1H, —CH—S—); 2.80 (dd, 2H, —$CH_2$—S—); 2.60 (s, 4H, —$CH_2$—CO—); 2.55 (s, 3H, —CO—$CH_3$); 2.50 (m, 2H, —$CH_2$—$CH_2$—CO—); 2.15 (m, 2H, —NH—); 1.40 (m, 6H, —$CH_2$—).

N-[3'-(1-Hydrazonoethyl)phenyl]-N'-(3,6-diamine-9-biotinoylaminononanyl)succinamide (Bio-(TETA)-Hy) (4)

The Bio-(TETA)-AP (3) (1.0 g; 1.71 mmol) is suspended in 25 ml of ethanol under hot conditions (60° C.). At reflux, hydrazine monohydrate (9 eq.; 750 µl) is added. The reaction is left at reflux for 2 h, and then cooled on ice. A precipitate forms after a short time. The two phases are separated and the precipitate is placed under vacuum. 690 mg of a flocculant solid are obtained (68%).

$^1$H NMR (200 MHz, DMSO-$d_6$) δ=9.95 (s, 1H, Ph-NH—CO—); 8.0 (s, 1H, —CO—NH—$CH_2$—); 7.90 (s, 1H); 7.80 (s, 1H, —$CH_2$—NH—CO—); 7.5 (d, 1H); 7.28 (m, 2H); 6.41 (s, 1H, —NH— biot); 6.36 (d, 3H, —NH— biot & —$NH_2$); 4.64 (t, 1H, —CH— biot); 4.30 (d, 1H, —CH— biot); 3.43 (m, 12H, —CH—NH—); 3.12 (m, 1H, —CH—S—); 2.80 (dd, 2H, —$CH_2$—S—); 2.60 (s, 4H, —CH—$C_2$—CO—); 2.50 (s, 3H, —CO—$CH_3$); 2.10 (m, 2H, —$CH_2$—NH—$CH_2$—); 1.50 (m, 6H, —$CH_2$—).

N-[3'-(1-Diazoethyl)phenyl]-N'-(3,6-diamine-9-biotinoylaminononanyl)succinamide (m-Bio-(TETA)-PMDAM) (5)

The Bio-(TETA)-Hy (4) (150 mg; 250.4 µmol) is solubilized in 1 ml of anhydrous DMSO under argon. It is left to react for 30 minutes with $MnO_2$ (s) (15 eq.; 330 mg) and then the mixture is filtered through a sintered glass funnel No. 4 with celite (0.5 cm thickness) and 3 Å molecular sieves (0.5 cm thickness). 100 µl are used for the NMR with the addition of 380 µl of DMSO-$d_6$ and 20 µl of methanol-$d_4$. The final volume is adjusted to 4.5 ml with anhydrous DMSO and 4% of methanol. The mixture is aliquoted in 250 µl-aliquots in a glovebox under argon. The compound is fuschia pink. The degree of purity (diazomethyl content) is verified by $^1$H NMR and UV-vis spectrophotometry (diazomethyl absorbance peak at 516 nm).

$^1$H NMR (200 MHz, DMSO-$d_6$) δ=9.93 (s, 1H, Ph-NH—CO—); 7.3 (s, 3H, $H_{aromatic}$); 6.6 (s, 1H, $H_{aromatic}$); 6.4 (s, 1H, —NH— biot); 6.3 (s, 1H, —NH— biot); 4.3 (t, 1H, —CH— biot); 3.3 (m, 12H, —$C_2$H—NH—); 3.3 (m, 1H, —CH—S—); 2.9 (dd, 2H, —$CH_2$—S—); 2.5 (4H, —$CH_2$—CO—); 2.1 (s, 3H, —$CH_3$); 2.0 (m, 2H, —$CH_2$—NH—$CH_2$—); 1.50 (m, 6H, —$CH_2$—).

EXAMPLE 3

Preparation of DNA and RNA Nucleic Acids

Example 3.1

Preparation of DNA Amplicons

The DNA amplicons are generated by PCR from *Mycobacterium tuberculosis* 16S genomic DNA targets ($10^{+4}$ copies as starting targets) using the Fast Start kit from Roche, 0.2 mM of each deoxyribonucleotide (d-ATP, d-CTP, d-GTP, d-TTP), 0.3 µM of primers and 0.4 µl of enzyme.

The PCR parameters are as follows:
−95° C.: 4 min then 35 cycles (95° C.: 30 sec; 55° C.: 30 sec; 72° C.: 30 sec) then 4° C.

The amplicons are analyzed qualitatively by agarose gel electrophoresis (1.5%, 0.5×TBE). The volume loaded is 5 µl and the migration is carried out for 20 min at 100 volts (V). The PCR products are visualized under a UV lamp after staining with ethidium bromide.

The conditions for the culturing, the extraction of the mycobacteria and also the amplification primers are given in patent application WO-A-99/65926.

Example 3.2

Preparation of Transcribed RNAs

The transcriptions are carried out from PCR target (Mycobacterium tuberculosis 16S RNA fragment) using the MEGAscript kit from Ambion: 7.5 mM of each nucleotide (ATP, CTP, GTP and UTP) and 2 µl of enzyme (RNA polymerase). The incubation time is 3 hours (h) at 37° C. The PCR amplification primers carry a T3 or T7 polymerase promoter, as described in application WO-A-99/65926 or in the article J. Clin Microbiol. 37(1), p 49-55, 1999, which makes it possible to carry out the transcription.

The transcripts are analyzed by agarose gel electrophoresis (1.5%; 0.5×TBE). The volume loaded is 5 µl and the migration is carried out for 20 min at 100V. The transcripts are visualized under a UV lamp after staining with ethidium bromide.

Identical results, from the point of view of the invention, can be obtained using other amplification techniques such as NASBA or TMA, which generate RNA amplicons directly.

The invention claimed is:

1. A temperature-stable labeling reagent of formula (0):

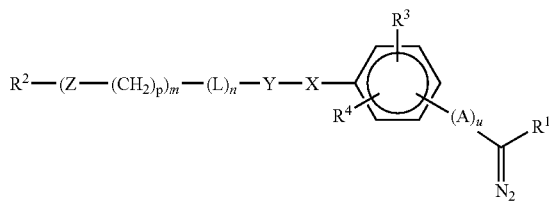

in which:
R$^1$ represents H or an alkyl, aryl or substituted aryl group,
R$^2$ represents a detectable label or at least two detectable labels interlinked by at least one multimeric structure, the detectable label being at least one label capable of directly or indirectly generating a detectable signal, and the detectable label being selected from the group consisting of an enzyme, a chromophore, a group with an electron density detectable by electron microscopy, a group with an electron density detectable by its electrical property, a radioactive molecule, and indirect systems,
L is a linker arm comprising a linear chain of at least two covalent bonds and n is an integer equal to 0 or 1,
R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, or —CO—NH—(CH$_2$)$_3$—(O—CH$_2$—CH$_2$)$_4$—CH$_2$—NH—R$^2$ with R=alkyl or aryl, A is a linker arm comprising at least one covalent double bond enabling the conjugation of the diazo function with the aromatic ring and u is an integer between 0 and 2,
—Y—X— represents —CONH—, —NHCO—, —CH$_2$O—, or —CH$_2$S—,
—Z— represents —NH—, —NHCO—, or —CONH—,
m is an integer between 2 and 10, and
p is an integer between 1 and 10.

2. The labeling reagent according to claim 1, of formula (1):

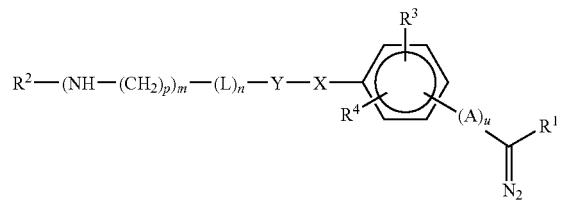

in which:
R$^1$ represents H or an alkyl, aryl or substituted aryl group,
R$^2$ represents a detectable label or at least two detectable labels interlinked by at least one multimeric structure,
L is a linker arm comprising a linear chain of at least two covalent bonds and n is an integer equal to 0 or 1,
R$^3$ and R$^1$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, or —CO—NH—(CH$_2$)$_3$—(O—CH$_2$—CH$_2$)$_4$—CH$_2$—NH—R$^2$ with R=alkyl or aryl, and
—Y—X— represents —CONH—, —NHCO—, —CH$_2$O—, or —CH$_2$S—,
m is an integer between 2 and 10, and
p is an integer between 1 and 10.

3. The reagent according to claim 2, wherein p is less than or equal to m.

4. The reagent according to claim 2, of formula (2):

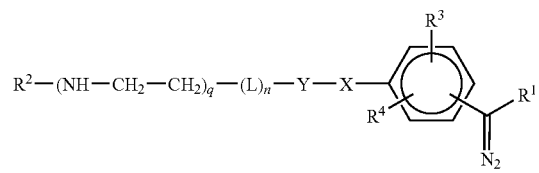

in which:
R$^1$ represents H or an alkyl, aryl or substituted aryl group,
R$^2$ represents a detectable label or at least two detectable labels interlinked by means of at least one multimeric structure,
L is a linker arm comprising a linear chain of at least two covalent bonds and n is an integer equal to 0 or 1,
R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, or —CO—NH—(CH$_2$)$_3$—(O—CH$_2$—CH$_2$)$_4$—CH$_2$—NH—R$^2$ with R=alkyl or aryl, and
q is an integer between 2 and 10.

5. The reagent, according to claim 4, of formula (3):

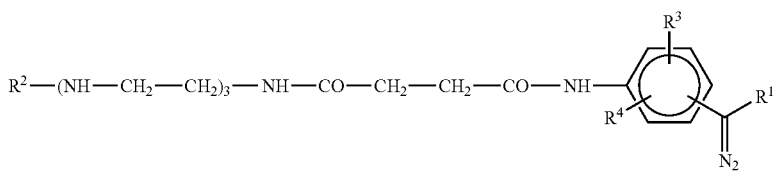

in which:
R$^1$ represents H or an alkyl, aryl or substituted aryl group,
R$^2$ represents a detectable label or at least two detectable labels interlinked by means of at least one multimeric structure,
R$^3$ and R$^4$ represent, independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, or —CO—NH—(CH$_2$)$_3$—(O—CH$_2$—CH$_2$)$_4$—CH$_2$—NH—R$^2$ with R=alkyl or aryl.

6. The reagent according to claim 5, wherein R$^2$ consists of a D-biotin residue of formula (4):

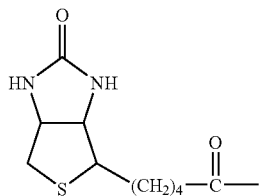

7. The reagent according to claim 6, wherein R$^1$ is CH$_3$, and R$^3$ and R$^4$ each represent H.

8. The reagent according to claim 4, in which the structure -(L)$_n$- consists of:
spermine or N,N'-bis(3-aminopropyl)-1,4-diaminobutane: NH$_2$—(CH$_2$)$_3$—NH—(CH$_2$)$_4$—NH—(CH$_2$)$_3$—NH$_2$, or
spermidine or N-(3-aminopropyl)-1,4-butanediamine: H$_2$N—(CH$_2$)$_4$—NH—(CH$_2$)$_3$—NH$_2$, or
a derivative containing an alanine motif: NH$_2$—CH$_2$—CH$_2$—COOH.

9. A temperature-stable labeling reagent of formula (6):

in which:
R$^2$ represents a detectable label or at least two detectable labels interlinked by at least one multimeric structure, the detectable label being at least one label capable of directly or indirectly generating a detectable signal, and the detectable label being selected from the group consisting of an enzyme, a chromophore, a group with an electron density detectable by electron microscopy, a group with an electron density detectable by its electrical property, a radioactive molecule, and indirect systems,
L is a linker arm comprising a linear chain of at least two covalent bonds and n is an integer equal to 0 or 1,
R$^3$ and R$^4$ represent independently of one another: H, NO$_2$, Cl, Br, F, I, R$^2$-(L)$_n$-Y—X—, OR, SR, NR$_2$, R, NHCOR, CONHR, COOR, —CO—NH—(CH$_2$)$_3$—(O—CH$_2$—CH$_2$)$_3$—CH$_2$—NH—R$^2$, or —CO—NH—(CH$_2$)$_3$—(O—CH$_2$—CH$_2$)$_4$—CH$_2$—NH—R$^2$ with R=alkyl or aryl,
A is a linker arm comprising at least one covalent double bond enabling the conjugation of the diazo function with the aromatic ring and u is an integer between 0 and 2,
—Y—X— represents —CONH—, —NHCO—, —CH$_2$O—, or —CH$_2$S—,
—Z— represents —NH—, —NHCO—, or —CONH—,
m is an integer between 2 and 10, and
p is an integer between 1 and 10.

10. The labeling reagent, according to claim 9, of formula (7):

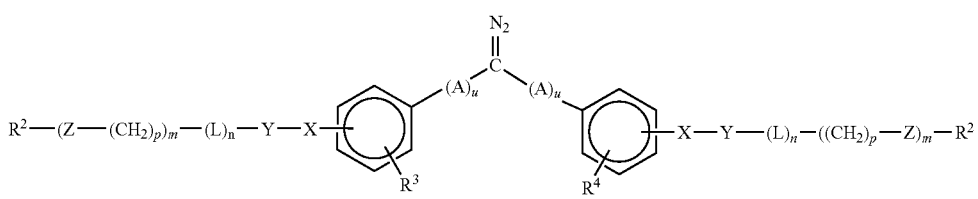

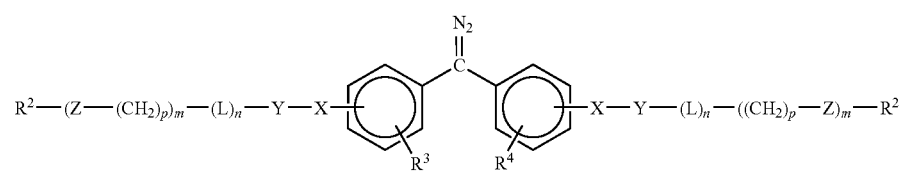

in which:
- R² represents a detectable label or at least two detectable labels interlinked by at least one multimeric structure,
- L is a linker arm comprising a linear chain of at least two covalent bonds and n is an integer equal to 0 or 1,
- R³ and R⁴ represent, independently of one another: H, NO₂, Cl, Br, F, I, R²-(L)ₙ-Y—X—, OR, SR, NR₂, R, NHCOR, CONHR, COOR, —CO—NH—(CH₂)₃—(O—CH₂—CH₂)₃—CH₂—NH—R², or —CO—NH—(CH₂)₃—(O—CH₂—CH₂)₄—CH₂—NH—R² with R=alkyl or aryl,
- —Y—X— represents —CONH—, —NHCO—, —CH₂O—, or —CH₂S—,
- —Z— represents —NH—, —NHCO—, or —CONH—,
- m is an integer between 2 and 10, and
- p is an integer between 1 and 10.

11. The reagent according to claim 1, wherein:
- L comprises a motif —(O—CH₂—CH₂)—, repeated from 1 to 20 times, and
- —Z— is —NH—, —NHCO— or —CONH—.

12. The reagent according to claim 9, wherein:
- L comprises a motif —(O—CH₂—CH₂)—, repeated from 1 to 20 times, and
- —Z— is —NH—, —NHCO— or —CONH—.

13. A method for the synthesis of a labeling reagent according to claim 1, comprising the following steps:
a) providing a label or a label precursor having a reactive function R⁶,
b) providing a linker arm of formula (8):

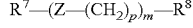

in which:
- —Z— represents —NH—, —NHCO—, or —CONH—,
- m is an integer between 2 and 10,
- p is an integer between 1 and 10,
- R⁷ and R⁸ represent two reactive functions which may be identical or different, c) reacting together the reactive function R⁶ of said label or label precursor and the function R⁷ the linker arm of formula (8) in the presence of at least one coupling agent to form a covalent bond, R⁶ and R⁷ being complementary, d) providing a derivative of formula (9):

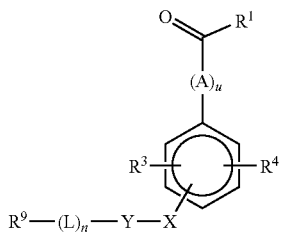

in which:
- R¹ represents H or an alkyl, aryl or substituted aryl group,
- L is a linker arm comprising a linear chain of at least two covalent bonds and n is an integer equal to 0 or 1,
- R³ and R⁴ represent, independently of one another: H, NO₂, Cl, Br, F, I, R²-(L)ₙ-Y—X—, OR, SR, NR₂, R, NHCOR, CONHR, COOR, —CO—NH—(CH₂)₃—(O—CH₂—CH₂)₃—CH₂—NH—R², or —CO—NH—(CH₂)₃—(O—CH₂—CH₂)₄—CH₂—NH—R² with R=alkyl or aryl,
- —Y—X— represents —CONH—, —NHCO—, —CH₂O—, or —CH₂S—,
- A is a linker arm comprising at least one covalent double bond enabling the conjugation of the diazomethyl function with the aromatic ring and u is an integer equal to 0 or 1, and
- R⁹ represents a reactive function complementary to R⁸, e) reacting together the reactive function R⁹ of the derivative of formula (9) and the function R⁸ of the linker arm of formula (8) in the presence of at least one coupling agent to form a covalent bond, f) reacting the hydrazine or one of its derivatives with the ketone or aldehyde function to form a hydrazone, and g) converting the hydrazone to a diazomethyl function by means of an appropriate treatment.

14. A method for the synthesis of a labeling reagent according to claim 9, comprising the following steps:
a) providing a label or a label precursor having a reactive function R⁶,
b) providing a linker arm of formula (8):

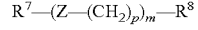

in which:
- —Z— represents —NH—, —NHCO—, or —CONH—,
- m is an integer between 2 and 10,
- p is an integer between 1 and 10,
- R⁷ and R⁸ represent two reactive functions which may be identical or different, c) reacting together the reactive function R⁶ of said label or label precursor and the function R⁷ the linker arm of formula (8) in the presence of at least one coupling agent to form a covalent bond, R⁶ and R⁷ being complementary, d) providing a derivative of formula (9):

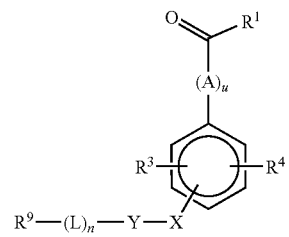

in which:
- R¹ represents H or an alkyl, aryl or substituted aryl group,
- L is a linker arm comprising a linear chain of at least two covalent bonds and n is an integer equal to 0 or 1,
- R³ and R⁴ represent, independently of one another: H, NO₂, Cl, Br, F, I, R²-(L)ₙ-Y—X—, OR, SR, NR₂, R, NHCOR, CONHR, COOR, —CO—NH—(CH₂)₃—(O—CH₂—CH₂)₃—CH₂—NH—R², or —CO—NH—(CH₂)₃—(O—CH₂—CH₂)₄—CH₂—NH—R² with R=alkyl or aryl,
- —Y—X— represents —CONH—, —NHCO—, —CH₂O—, or —CH₂S—,
- A is a linker arm comprising at least one covalent double bond enabling the conjugation of the diazomethyl function with the aromatic ring and u is an integer equal to 0 or 1, and
- R⁹ represents a reactive function complementary to R⁸, e) reacting together the reactive function R⁹ of the derivative of formula (9) and the function R⁸ of the linker arm of formula (8) in the presence of at least one coupling agent to form a covalent bond, f) reacting the hydrazine or one of its derivatives with the ketone or aldehyde function to form a hydrazone, and g) converting the hydrazone to a diazomethyl function by means of an appropriate treatment.

15. The method of synthesis according to claim 13, further comprising:
an additional step consisting of protection of the ketone or aldehyde function of compound (9), and
a subsequent additional step consisting of deprotection of said ketone or aldehyde function.

16. The method of synthesis according to claim 14, further comprising:
an additional step consisting of protection of the ketone or aldehyde function of compound (9), and
a subsequent additional step consisting of deprotection of said ketone or aldehyde function.

17. A method for the labeling of a biological molecule, comprising bringing into contact, in a homogeneous solution in a substantially aqueous buffer, the biological molecule and a reagent according to claim 1.

18. A method for the labeling of a biological molecule, comprising bringing into contact, in homogeneous solution in a substantially aqueous buffer, a biological molecule and a reagent according to claim 9.

19. A labeled biological molecule which can be obtained by the method according to claim 17.

20. A labeled biological molecule which can be obtained by the method according to claim 18.

21. A method for the labeling and fragmentation of a single-stranded or double-stranded nucleic acid, the method comprising:
fragmenting the nucleic acid,
attaching a label to at least one of the fragments by means of a labeling reagent chosen from the reagents according to claim 1,
said reagent coupling covalently and predominantly on at least one phosphate of said fragment.

22. A method for the labeling and fragmentation of a single-stranded or double-stranded nucleic acid, the method comprising:
fragmenting the nucleic acid,
attaching a label to at least one of the fragments by means of a labeling reagent chosen from the reagents according to claim 9,
said reagent coupling covalently and predominantly on at least one phosphate of said fragment.

23. The method according to claim 21, wherein the labeling reagent is chosen from the compounds of formula (3):

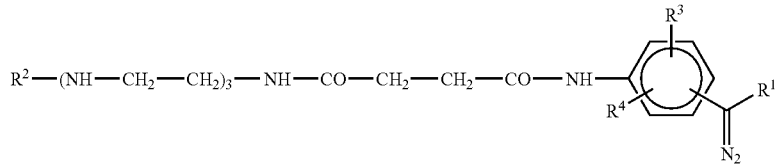

in which:
$R^1$ represents H or an alkyl, aryl or substituted aryl group,
$R^2$ represents a detectable label or at least two detectable labels interlinked by at least one multimeric structure,
L is a linker arm comprising a linear chain of at least two covalent bonds and n is an integer equal to 0 or 1, and
$R^3$ and $R^4$ represent, independently of one another: H, $NO_2$, Cl, Br, F, I, $R^2$-$(L)_n$-Y—X—, OR, SR, $NR_2$, R, NHCOR, CONHR, COOR, —CO—NH—$(CH_2)_3$—(O—$CH_2$—$CH_2)_3$—$CH_2$—NH—$R^2$, or —CO—NH—$(CH_2)_3$—(O—$CH_2$—$CH_2)_4$—$CH_2$—NH—$R^2$ with R=alkyl or aryl.

24. The method according to claim 22, wherein the labeling reagent is chosen from the compounds of formula (3):

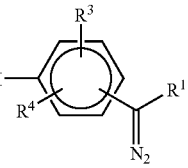

in which:
$R^1$ represents H or an alkyl, aryl or substituted aryl group,
$R^2$ represents a detectable label or at least two detectable labels interlinked by at least one multimeric structure,
L is a linker arm comprising a linear chain of at least two covalent bonds and n is an integer equal to 0 or 1, and
$R^3$ and $R^4$ represent, independently of one another: H, $NO_2$, Cl, Br, F, I, $R^2$-$(L)_n$-Y—X—, OR, SR, $NR_2$, R, NHCOR, CONHR, COOR, —CO—NH—$(CH_2)_3$—(O—$CH_2$—$CH_2)_3$—$CH_2$—NH—$R^2$, or —CO—NH—$(CH_2)_3$—(O—$CH_2$—$CH_2)_4$—$CH_2$—NH—$R^2$ with R=alkyl or aryl.

25. The method according to claim 23, wherein the fragmentation and the labeling are carried out in two steps.

26. The method according to claim 24, wherein the fragmentation and the labeling are carried out in two steps.

27. The method according to claim 23, wherein the fragmentation and the labeling are carried out in one step.

28. The method according to claim 24, wherein the fragmentation and the labeling are carried out in one step.

29. The method according to claim 25, wherein the labeling is carried out in a substantially aqueous homogeneous solution.

30. The method according to claim 27, wherein the labeling is carried out in a substantially aqueous homogeneous solution.

31. The method according to claim 26, wherein the labeling is carried out in a substantially aqueous homogeneous solution.

32. The method according to claim 25, wherein the fragmentation is carried out by an enzymatic, physical, or chemical process.

33. The method according to claim 26, wherein the fragmentation is carried out by an enzymatic, physical, or chemical process.

34. A labeled nucleic acid obtained by the method according to claim 21.

35. A labeled nucleic acid obtained by the method according to claim 22.

36. A kit for the detection of a target nucleic acid, comprising a labeled nucleic acid according to claim 34.

37. A kit for the detection of a target nucleic acid, comprising a labeled nucleic acid according to claim 35.

38. A solid support to which is attached a reagent according to claim 1.

39. A solid support to which is attached a reagent according to claim 9.

40. A method for the capture of nucleic acids, comprising:
providing a solid support to which is directly or indirectly attached at least one biological molecule according to claim 19, the biological molecule or the nucleic acid comprising a diazomethyl function,
bringing into contact a biological sample which may contain free nucleic acids, and
washing the solid support where the molecule(s) is (are) covalently attached at least to a nucleic acid.

41. A method for the capture of nucleic acids, comprising the following steps:
providing a solid support to which is directly or indirectly attached at least one biological molecule according to claim 20, the biological molecule or the nucleic acid comprising a diazomethyl function,
bringing into contact a biological sample which may contain free nucleic acids, and
washing the solid support where the molecule(s) is (are) covalently attached at least to a nucleic acid.

* * * * *